(12) United States Patent
Gunaratnam et al.

(10) Patent No.: US 8,796,456 B2
(45) Date of Patent: Aug. 5, 2014

(54) NAPHTHALENE DIIMIDE COMPOUNDS

(75) Inventors: Mekala Gunaratnam, London (GB); Francisco Cuenca, Valencia (ES); Stephen Neidle, London (GB)

(73) Assignee: University College London, London (GB)

( * ) Notice: Subject to any disclaimer, the term of this patent is extended or adjusted under 35 U.S.C. 154(b) by 699 days.

(21) Appl. No.: 12/745,431

(22) PCT Filed: Nov. 28, 2008

(86) PCT No.: PCT/GB2008/051131
§ 371 (c)(1),
(2), (4) Date: May 28, 2010

(87) PCT Pub. No.: WO2009/068916
PCT Pub. Date: Jun. 4, 2009

(65) Prior Publication Data
US 2010/0311739 A1 Dec. 9, 2010

(30) Foreign Application Priority Data
Nov. 29, 2007 (GB) .................................. 0723439.6

(51) Int. Cl.
*C07D 519/00* (2006.01)
*A61K 31/4412* (2006.01)

(52) U.S. Cl.
USPC ........................................... 546/68; 514/288

(58) Field of Classification Search
USPC ................................. 514/210.21, 288; 546/68
See application file for complete search history.

(56) References Cited

U.S. PATENT DOCUMENTS

2003/0153005 A1  8/2003  Schmid et al.

FOREIGN PATENT DOCUMENTS

| DE | 661756 C | 6/1938 |
|----|----------|--------|
| GB | 1124536  | * 8/1968 |
| GB | 1124536 A | 8/1968 |

OTHER PUBLICATIONS

Benzo[lmn] [3,8]phenanthroline-1,3,6,8 (2H, 7H)-tetrone, 2,7-bis (2-hydroxyethyl)-4, 9-bis [(2-hydroxyethyl)amino]. Retrieved from Database Registry Chemical Abstract Service 2001; STN Database: Accession No. 321942-77-2.*

Bondarenko, E. F. et al. Studies of naphthalene-1, 4, 5, 8-tetracarboxylic acid derivatives. I. Naphathalene-1, 4, 5-8-tetracarboxylic acid bisimides. Retrieved from Database Caplus Chemical Abstract Service; STN Database: Accession No. 1980:215109.

Benzo[lmn] [3, 8] phenanthroline-1, 3, 6, 8 (2H, 7H)-tetrone, 2, 7-bis (2-hydroxyethyl)-4, 9-bis [ (2-hydroxyethyl)amino ]. Retrieved from Database Registry Chemical Abstract Service 2001; STN Database: Accession No. 321942-77-2.

Sissi et al. (2007). Tri-, tetra-, and heptacylcic perylene analogues as new potential antineoplastic agents based on DNA telomerase inhibition. *Bioorganic & Medicinal Chemistry*, 15(1): 555-562. Elsevier Science Ltd. GB.

Brana, M. F. et al. (2001). Naphthalimides as anti-cancer agents: Synthesis and biological activity. *Current Medicinal Chemistry-Anti-Cancer Agents*, 1(3): 237-255. Bentham Science Publishers Ltd. Hilversum, NL.

Quaquebeke, E. V. et al. (2007). 2, 2, 2-Trichloro-N-( { 2-[2-(dimethylamino)ethyl]-1, 3-dioxo-2, 3-dihydro-1H-benzo[de]isoquinolin- 5-yl}carbamoyl)acetamide (UNBS3157), a Novel Nonhematotoxic Naphthalimide Deriviative with Potent Antitumor Activity. *Journal of Medicinal Chemistry*, 50(17): 4122-4134.

* cited by examiner

*Primary Examiner* — Yong Chu
*Assistant Examiner* — Sonya Wright
(74) *Attorney, Agent, or Firm* — Saliwanchik, Lloyd & Eisenschenk

(57) ABSTRACT

The invention relates to novel compounds which are naphthalene diimides of general formula (I). The compounds are used in therapy, particularly in cancer treatment.

30 Claims, 5 Drawing Sheets

NAPHTHALENE DIIMIDE COMPOUNDS

CROSS-REFERENCE TO RELATED APPLICATIONS

Figure 1:
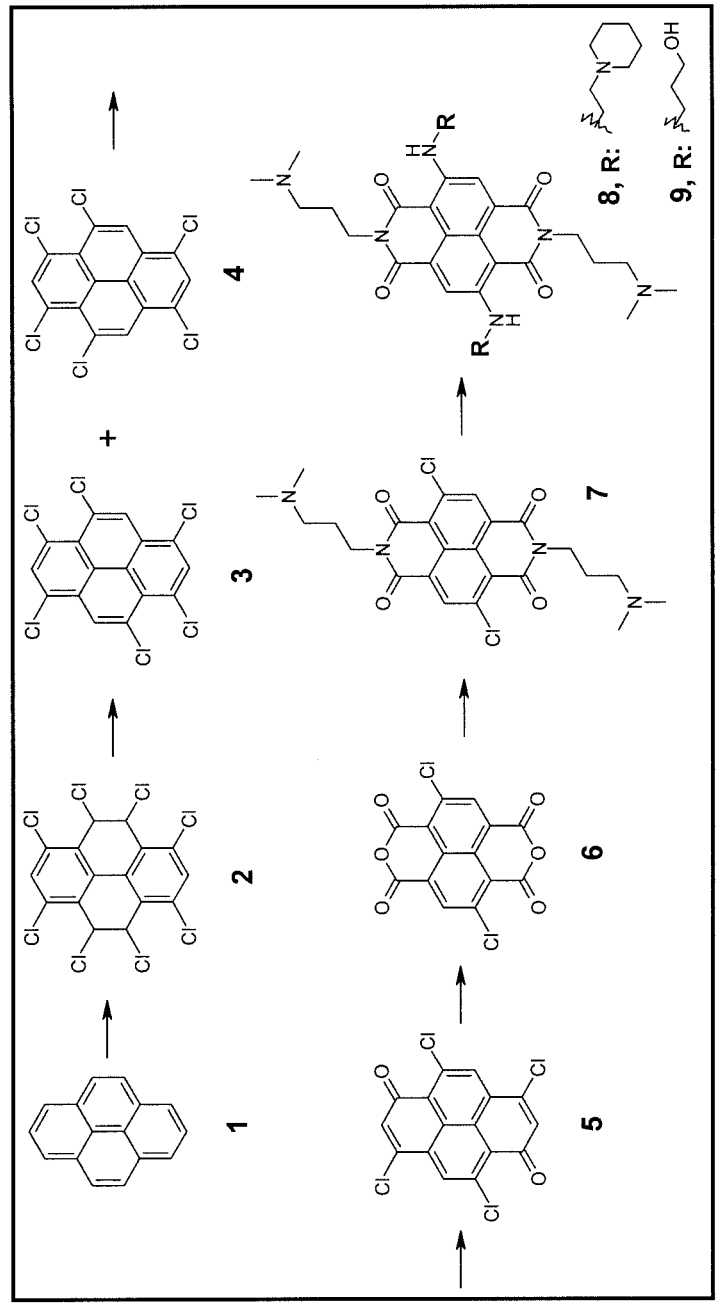

This application is the U.S. national stage application of International Patent Application No. PCT/GB2008/051131, filed Nov. 28, 2008, which claims priority to Great Britain Application No. 0723439.6, filed Nov. 29, 2007, the disclosures of each of which are incorporated herein by reference in their entirety.

The present invention relates to novel compounds which are naphthalene diimides, more particularly tri- and tetra-substituted naphthalene diimides. The invention also concerns pharmaceutical compositions comprising the novel compounds and their use in therapy, particularly in cancer treatment.

Telomeres are highly specialised DNA-protein structures that form the end of chromosomes. Telomere integrity is required for a cell to remain viable. The enzyme telomerase maintains telomere length and is over-expressed in around 90% of all cancer types, and therefore in recent years this enzyme has become a common target in cancer therapeutics. Telomerase can be inhibited by inducing telomeric DNA to form G-quadruplex structures, which cannot be accessed by the enzyme.

G-quadruplexes are also present in the promoter regions of some genes and can regulate gene expression by disrupting the transcription mechanism.

Naphthalene imide and diimide derivatives (NDs) have been shown to interact with duplex (DNA) [1]. Disubstituted NDs have been screened as G-quadruplex ligands, but showed limited affinity [2]. In [2], the molecular structure of the majority of text compounds was as follows:

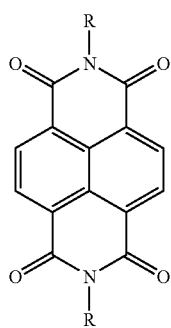

wherein R is an amine such as $(CH_2)_2N(CH_3)_2$.

The researchers in [3] describe the use of some naphthalimides as anti-cancer agents. The naphthalimide nitrogen is substituted with a wide range of groups including tertiary amines. However, no naphthalene diimide compounds are synthesised.

In view of the prior art, there is a need to provide improved anti-cancer agents. In particular, there is a need to provide further naphthalene diimide derivatives which have improved G-quadruplex binding ability and anti-cancer effects.

In view of the above, there is provided in a first aspect of the invention a compound of general formula (I) or a pharmaceutically acceptable salt or prodrug thereof

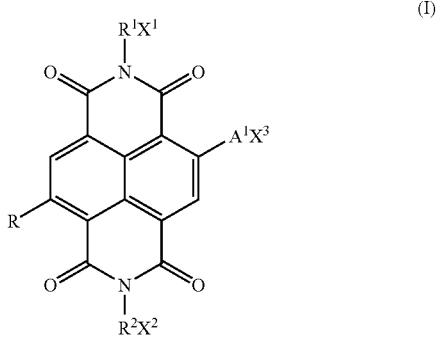

wherein $R^1$ and $R^2$ are each independently divalent radicals derived from $C_{1-20}$ alkyl, $C_{2-20}$ alkenyl, $C_{7-20}$ alkaryl, $C_{2-10}$ alkynyl, $C_{7-20}$ aralkyl, $C_{2-20}$ heteroaralkyl, $C_{3-30}$ heterocyclylalkyl, $C_{3-30}$ alkylheterocyclyl, $C_{3-20}$ cycloalkyl, $C_{3-20}$ heterocyclyl, $C_{2-20}$ heteroaryl, $C_{6-20}$ aryl or $C_{1-10}$ alkoxy;

R is H or $A^2X^4$;

wherein $X^1$-$X^4$ are each independently selected from halo, OH, $OR^3$, COH, $NH_2$, $NHR^3$, $NR^3R^4$, COOH, $CONH_2$, $COOR^3$, $CONHR^3$, $CONR^3R^4$, SH, $SR^3$, $COR^3$ or cyano;

wherein $R^3$ and $R^4$ are independently selected from $C_{1-6}$ alkyl, $C_{6-20}$ aryl, $C_{7-20}$ aralkyl or $R^3$ and $R^4$ together with the nitrogen atom to which they are attached form a 3-8 membered ring, which is optionally substituted and optionally comprises other hetero atoms;

$A^1$ and $A^2$ are each independently selected from $NHR^5$;

wherein $R^5$ is a divalent radical derived from $C_{1-20}$ alkyl, $C_{6-20}$ aryl, $C_{7-20}$ alkaryl or $C_{7-20}$ aralkyl;

wherein any of the groups $R^1$-$R^5$, $A^1$ and $A^2$ may be substituted with $C_{1-20}$ alkyl, $C_{2-20}$ alkenyl, $C_{7-20}$ alkaryl, $C_{2-10}$ alkynyl, $C_{7-20}$ aralkyl, $C_{2-20}$ heteroaralkyl, $C_{3-30}$ heterocyclylalkyl, $C_{3-30}$ alkylheterocyclyl, $C_{3-20}$ cycloalkyl, $C_{3-20}$ heterocyclyl, $C_{2-20}$ heteroaryl, $C_{6-20}$ aryl or $C_{1-10}$ alkoxy, halo, OH, $OR^3$, COH, $NH_2$, $NHR^3$, $NR^3R^4$, COOH, $CONH_2$, $COOR^3$, $CONHR^3$, $CONR^3R^4$, SH, $SR^3$, $COR^3$ or cyano.

Also provided, in a second aspect of the invention is a pharmaceutical composition comprising a compound of general formula (I) or a pharmaceutically acceptable salt or prodrug thereof.

The third aspect of the invention provides a compound of general formula (I), or a salt, solvate or pro-drug of general formula (I), for use in therapy.

The final aspect of the invention provides use of a compound of general formula (I), or a salt, solvate or pro-drug thereof, or a pharmaceutical composition as defined above, in the manufacture of a medicament for prophylaxis or treatment of cancer.

The use of substituted naphthalene diimides as dyes is well known. The compounds have extensively conjugated structures which makes them excellent fluorescent colorants. For instance, [4] discloses compounds which may be substituted on the aryl rings as well as on the nitrogen atoms of the imide groups. However, the compounds in this reference have simple alkyl or aryl chains attached to the imide nitrogens, and do not have groups corresponding to $X^1$-$X^4$ of the present invention. Similarly, [5] discloses naphthalene 1,4,5,8 tetra-carboxylic bisimides which may be substituted on the ring (see substituents X and Y on the structure below):

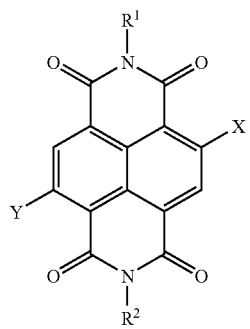

In these compounds, neither of X, nor Y, can be hydrogen. There are no specific Examples of compounds with groups $A^1X^3$ and $A^2X^4$ according to the present invention. The compounds in [5] are used as fluorescent and laser dyes.

The compounds of the present invention have been shown to be able to stabilise G-quadruplex regions in DNA to a greater extent than the anti-cancer agents of the prior art.

The compounds have also been shown to have better selectivity towards the G-quadruplex rather than duplex DNA, in comparison to the disubstituted naphthalene diimides already tested and reported in the literature. The novel compounds of this invention therefore have great potential as anti-cancer drugs.

Compounds according to the first aspect of the invention, of general formula (I), may be either tri- or tetrasubstituted. Accordingly, when the compounds are tri-substituted, R is hydrogen. Tetrasubstituted compounds wherein R is $A^2X^4$, are preferred, however, since these have been found to have a greater stabilisation effect on quadruplex DNA.

The groups represented by $R^1X^1$, $A^1X^3$, $R^2X^2$ and $A^2X^4$ may be the same or different. In a preferred embodiment of the invention, $R^1X^1$ is the same as $R^2X^2$. Similarly it is preferred that $X^1X^3$ is the same as $X^2X^4$.

Any of $X^1$-$X^4$ may be halo. By halo is meant a halogen radical such as fluoro, chloro, bromo or iodo. Preferably, the halo is chloro or bromo.

It is preferred that the groups $X^1$-$X^4$ comprise a group which is ionisable. Accordingly, particularly preferred groups for $X^1$-$X^4$ are $NH_2$, $NR^3R^4$, OH, $OR^3$ and $NHR^3$. In particular, groups that are protonated at physiological pH are preferred, for instance, primary, secondary or tertiary amines. Typically, at least one of the groups $X^1$-$X^4$ is a tertiary amine, for instance dimethylamine or diethylamine.

In one embodiment, any or all of $X^1$-$X^4$ are $NR^3R^4$, wherein $R^3$ and $R^4$ together with the nitrogen to which they are attached form a 5-8 membered ring, typically a 5 or 6 membered ring. The ring may contain atoms other than carbon (and the nitrogen) atoms, for instance, it may contain an oxygen atom. The ring $NR^3R^4$ is preferably pyrrolidine, piperidine or morpholine.

With regards to the groups $R^1$ and $R^2$, these are preferably linkers which act to space the groups $X^1$ and $X^2$ from the naphthalene diimide core. Typically, $R^1$ and $R^2$ are each, independently divalent radicals (generated by removal of H from C—H) selected from $C_{1-20}$ alkyl, preferably $C_{2-4}$ alkyl.

$A^1$ and $A^2$ are groups which link the naphthalene diimide core with groups $X^3$ and $X^4$. Generally, these groups $A^1$ and $A^2$ are of general formula $NHR^5$, wherein $R^5$ is a divalent radical derived from $C_{1-10}$ alkyl, preferably $C_{2-4}$ alkyl.

In a preferred embodiment of the invention, at least one of $A^1X^3$ and $A^2X^4$ have structure:

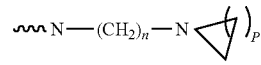

wherein n is 1-10, preferably 1-4, and p is 2-6.

Preferably, $R^5$, when present is identical to $R^1$ and $R^2$. Thus a particularly preferred group of compounds of this invention has general formula:

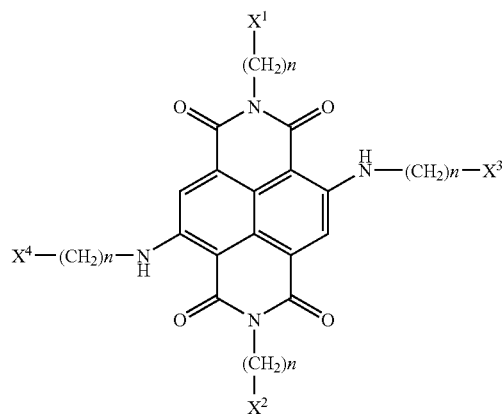

wherein each n is independently, 1-10, preferably 1-4.

Particularly preferred compounds are as follows:

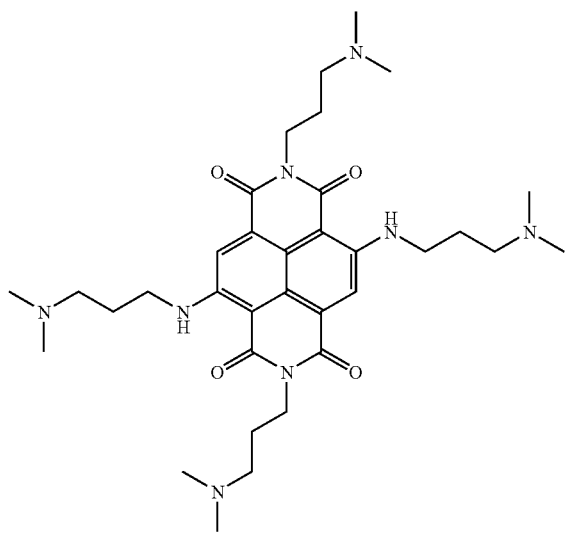

12

14
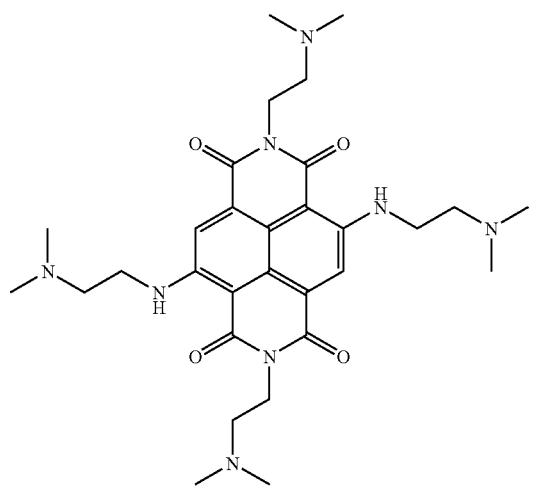
16
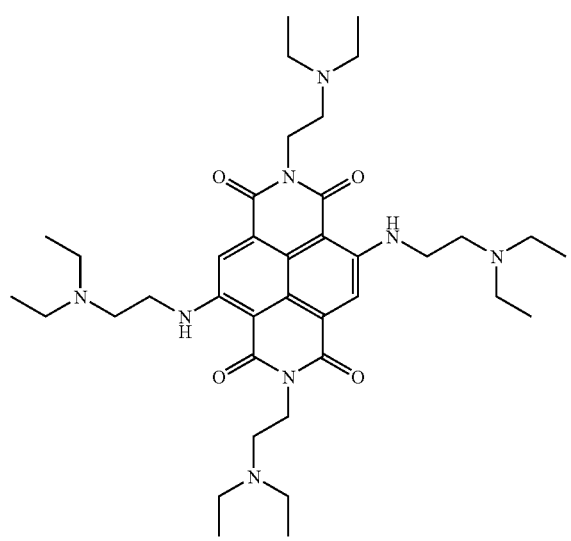
20
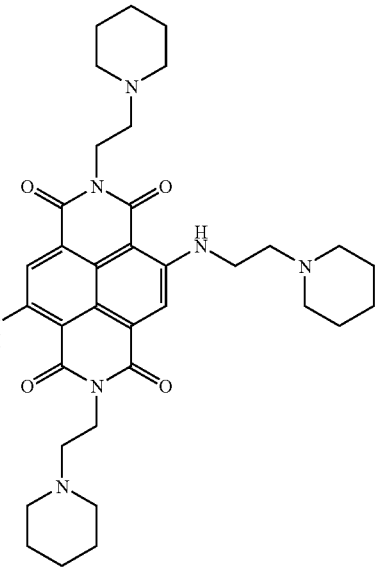
22
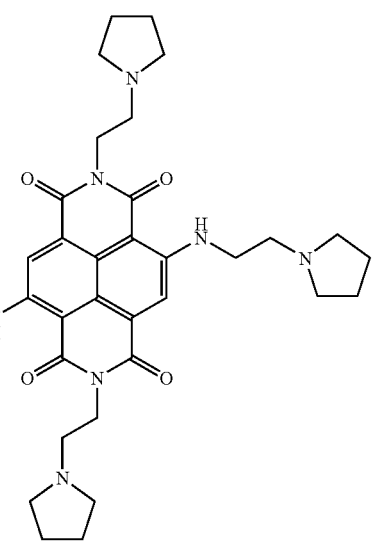
24
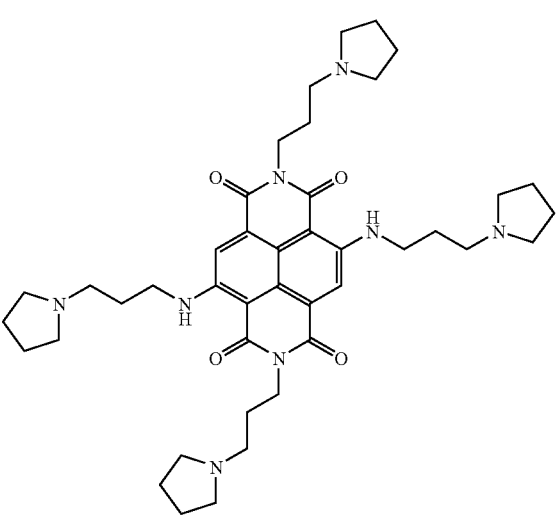

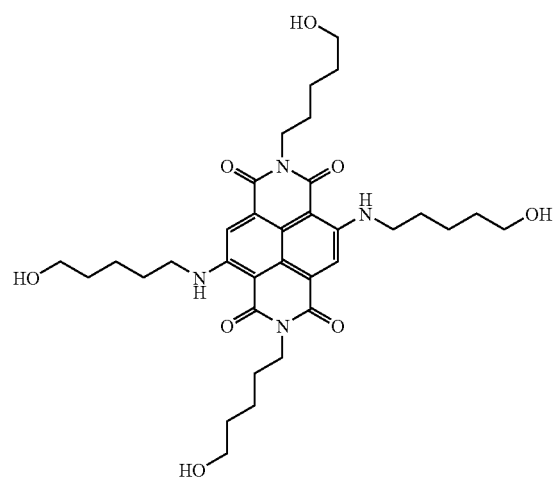
26
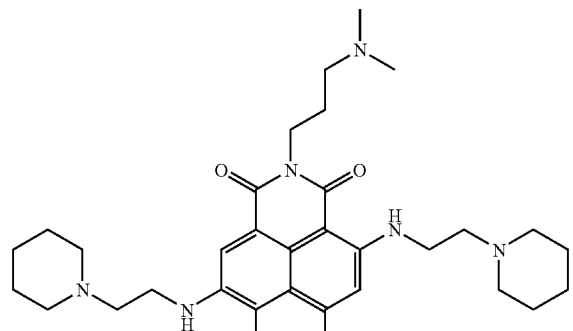
8
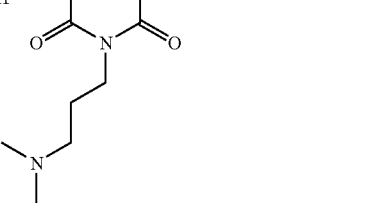
9
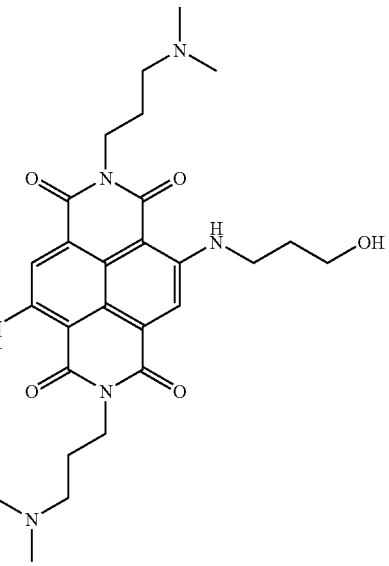
28
30
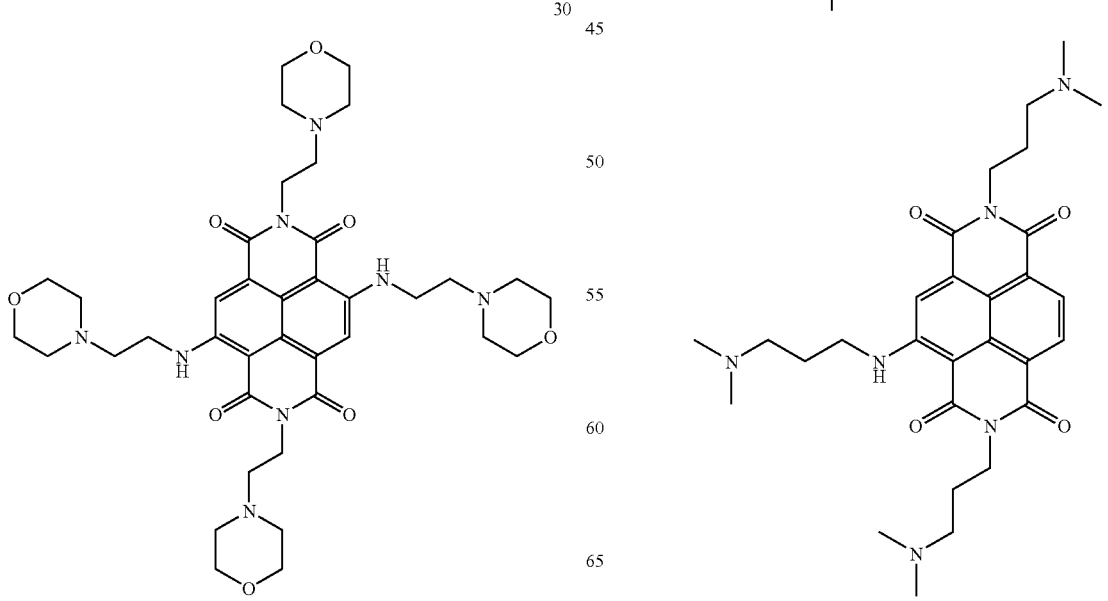
13

9
-continued
15
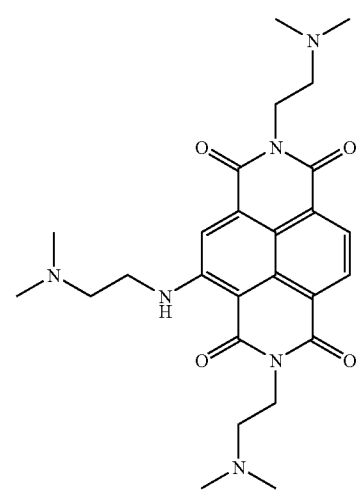
17
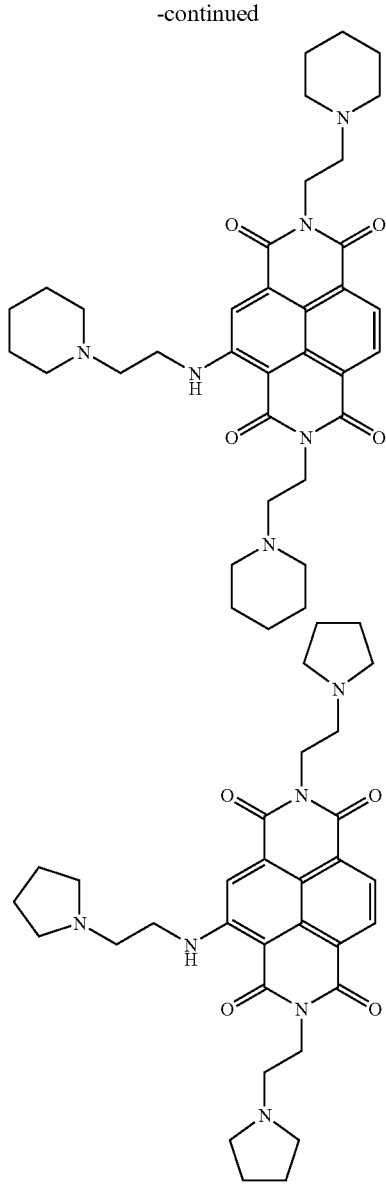
19
10
-continued
21
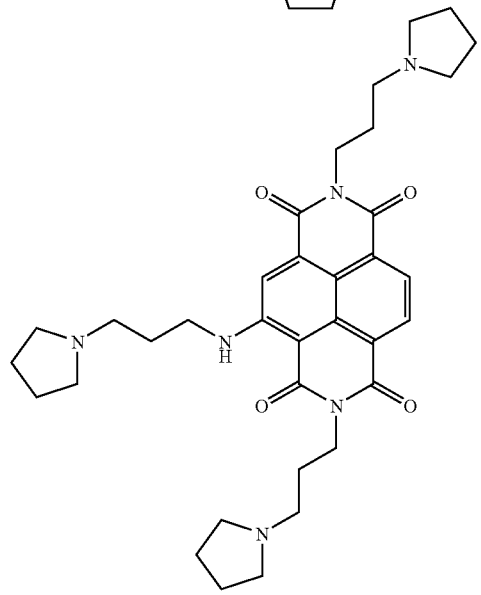
23
25

27

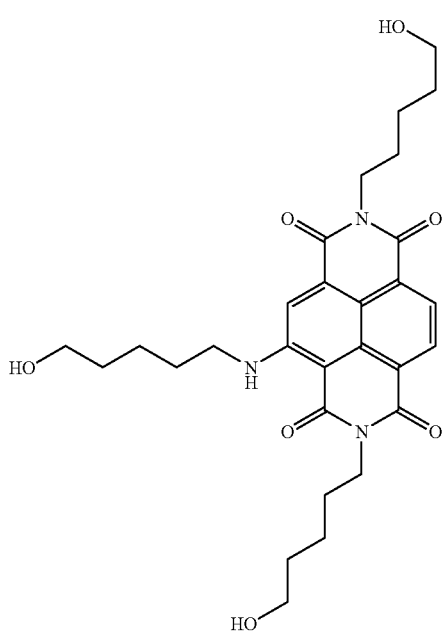

29

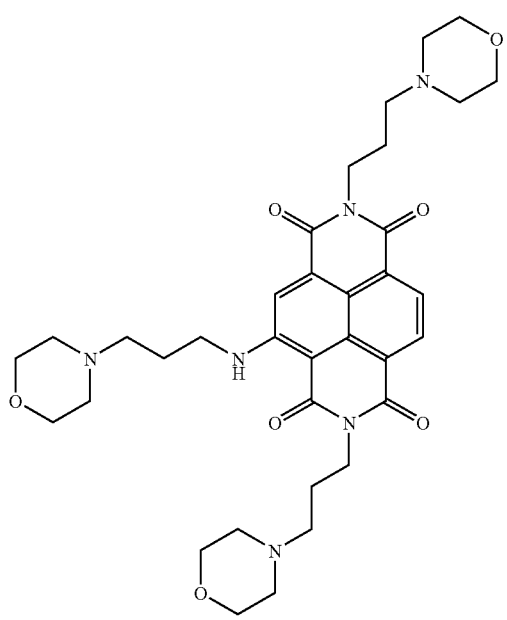

31

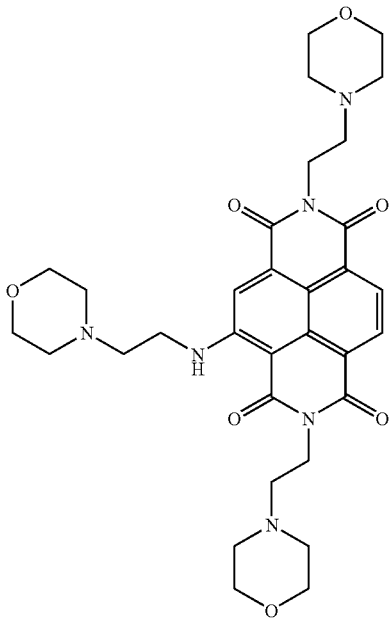

The present invention also provides the use of a compound of formula (I), or a salt, solvate or pro-drug thereof, substantially as described herein before, in the manufacture of a medicament for the prophylaxis or treatment of cancer.

The compounds of the present invention may be present in the form of pharmaceutical acceptable salts. Pharmaceutically acceptable salts of the acidic or basic compounds of the invention can of course be made by conventional procedures, such as by reacting the free base or acid with at least a stoichiometric amount of the desired salt-forming acid or base.

Pharmaceutically acceptable salts of the acidic compounds of the invention include salts with inorganic cations such as sodium, potassium, calcium, magnesium, zinc, and ammonium, and salts with organic bases. Suitable organic bases include N-methyl-D-glucamine, arginine, benzathine, diolamine, olamine, procaine and tromethamine.

Pharmaceutically acceptable salts of the basic compounds of the invention include salts derived from organic or inorganic acids. Suitable anions include acetate, adipate, besylate, bromide, camsylate, chloride, citrate, edisylate, estolate, fumarate, gluceptate, gluconate, glucuronate, hippurate, hyclate, hydrobromide, hydrochloride, iodide, isethionate, lactate, lactobionate, maleate, mesylate, methylbromide, methylsulfate, napsylate, nitrate, oleate, pamoate, phosphate, polygalacturonate, stearate, succinate, sulfate, sulfosalicylate, tannate, tartrate, terephthalate, tosylate and triethiodide. Hydrochloride salts of compound (I) are particularly preferred.

The compounds of general formula (I) may be prodrugs, that is compounds which are converted into the active drug at an appropriate target location in the human or animal body. For instance, when any or all of the groups $X^1$-$X^4$ are amines, $NR^3R^4$, the amine may be oxidised to form an N-oxide, $N^+(-O^-)R^3R^4$, which is a prodrug and can be bioreduced in hypoxic tissue.

Pro-drug forms of the pharmacologically-active compounds of the invention may be compounds according to formula (I) having an acid group which is esterified or amidated. Included in such esterified acid groups are groups of the form —C(C)OR$^a$, wherein R$^a$ is C$_{1-6}$ alkyl, phenyl, substituted phenyl, benzyl, substituted benzyl, or one of the following:

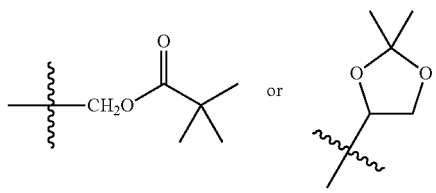

Amidated acid groups include groups of the formula —CONR$^b$R$^c$, wherein R$^b$ is H, C$_{1-5}$ alkyl, phenyl, substituted phenyl, benzyl, or substituted benzyl, and R$^c$ is —OH or one of the groups just recited for R$^b$.

Compounds of formula (I) having an amino group may be derivatised with a ketone or an aldehyde such as formaldehyde to form a Mannich base. This will hydrolyse with first order kinetics in aqueous solution.

It is anticipated that the compounds of the invention can be administered to a patient in need thereof by oral or parenteral routes, including intravenous, intramuscular, intraperitoneal, subcutaneous, rectal and topical administration, and inhalation.

For oral administration, the compounds of the invention will generally be provided in the form of tablets or capsules or as an aqueous solution or suspension.

Tablets for oral use may include the active ingredient mixed with pharmaceutically acceptable excipients such as inert diluents, disintegrating agents, binding agents, lubricating agents, sweetening agents, flavouring agents, colouring agents and preservatives. Suitable inert diluents include sodium and calcium carbonate, sodium and calcium phosphate and lactose. Corn starch and alginic acid are suitable disintegrating agents. Binding agents may include starch and gelatine. The lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatine capsules in which the active ingredient is mixed with a solid diluent and soft gelatine capsules wherein the active ingredient is mixed with water or an oil such as peanut oil, liquid paraffin or olive oil.

For intramuscular, intraperitoneal, subcutaneous and intravenous use, the compounds of the invention will generally be provided in sterile aqueous solutions or suspensions, buffered to an appropriate pH and isotonicity. Suitable aqueous vehicles include Ringer's solution and isotonic sodium chloride. Aqueous suspensions according to the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

The compounds of the present invention may be used in the treatment of a disease. The disease may be selected from the group consisting of cardiovascular diseases, disorders of the peripheral and central nervous system, inflammation, urological diseases, developmental disorders, cancer, metabolic diseases, viral, bacterial and endocrinological diseases and disorders of the gastroenterology system in a mammal.

In particular, the disease may be a parathyroid gland adenoma, parathyroid gland hyperplasia, parathyroid gland carcinoma, squamous carcinoma, renal carcinoma, breast carcinoma, prostate carcinoma, lung carcinomas, osteosarcomas, clear cell renal carcinoma, prostate cancer, lung cancer, breast cancer, gastric cancer, ovarian cancer, bladder cancer, leukaemias, melanomas, lymphomas or gliomas. Typically the compounds of the invention are used to treat gastric cancer.

In the treatment, a therapeutically effective amount of a compound of general formula (I), or a salt, solvate or producing thereof, is administered to a patient in need thereof.

The synthetic route to the novel compounds of this invention is based on a synthesis described in [4]. By "side chains" we mean the groups R$^1$X$^1$, R$^2$X$^2$, A$^1$X$^3$ and A$^2$X$^2$. Generally the compounds are synthesised in one or two steps from key intermediates, 2,6-dibromo-1,4,5,8-naphthalene tetracarboxylic acid dianhydride [A] or 2,6-dichloro-1,4,5,8-naphthalene tetra-carboxylic acid dianhydride [B]. See scheme 1 below:

Scheme 1

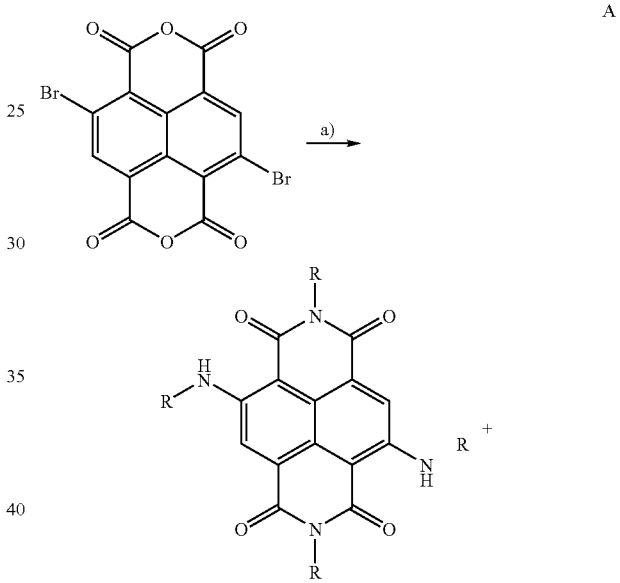

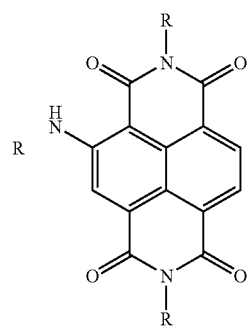

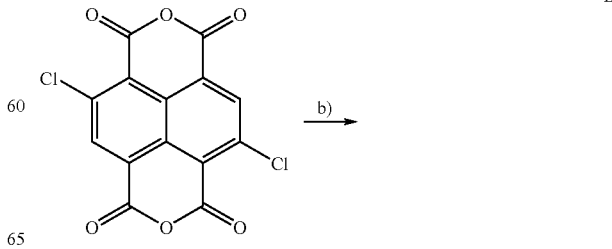

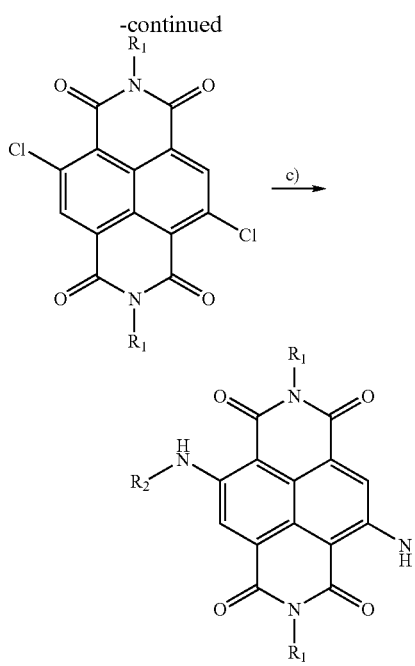

The tetrasubstituted analogues containing four identical side chains may be synthesised from either A or B using neat amine as a solvent and heating at 150° C. for around 10 minutes, for instance in a microwave. The more economical dibromo compound A is preferentially used as a starting material. Trisubstituted (and occasionally disubstituted) analogues are typically obtained as subproducts in the reactions using A. It is thought that the occurrence of these subproducts is due to radical debromination of the starting materials or intermediates caused by traces of DBI (dibromoisocyanuric acid) used in the previous synthetic step.

Compound B is preferably used for the synthesis of compounds which have different side chains. For this two-step synthesis compound B can be treated with a first amine in acetic acid and subsequently with a second amine, which substitutes the chlorine radicals.

Figure 2:
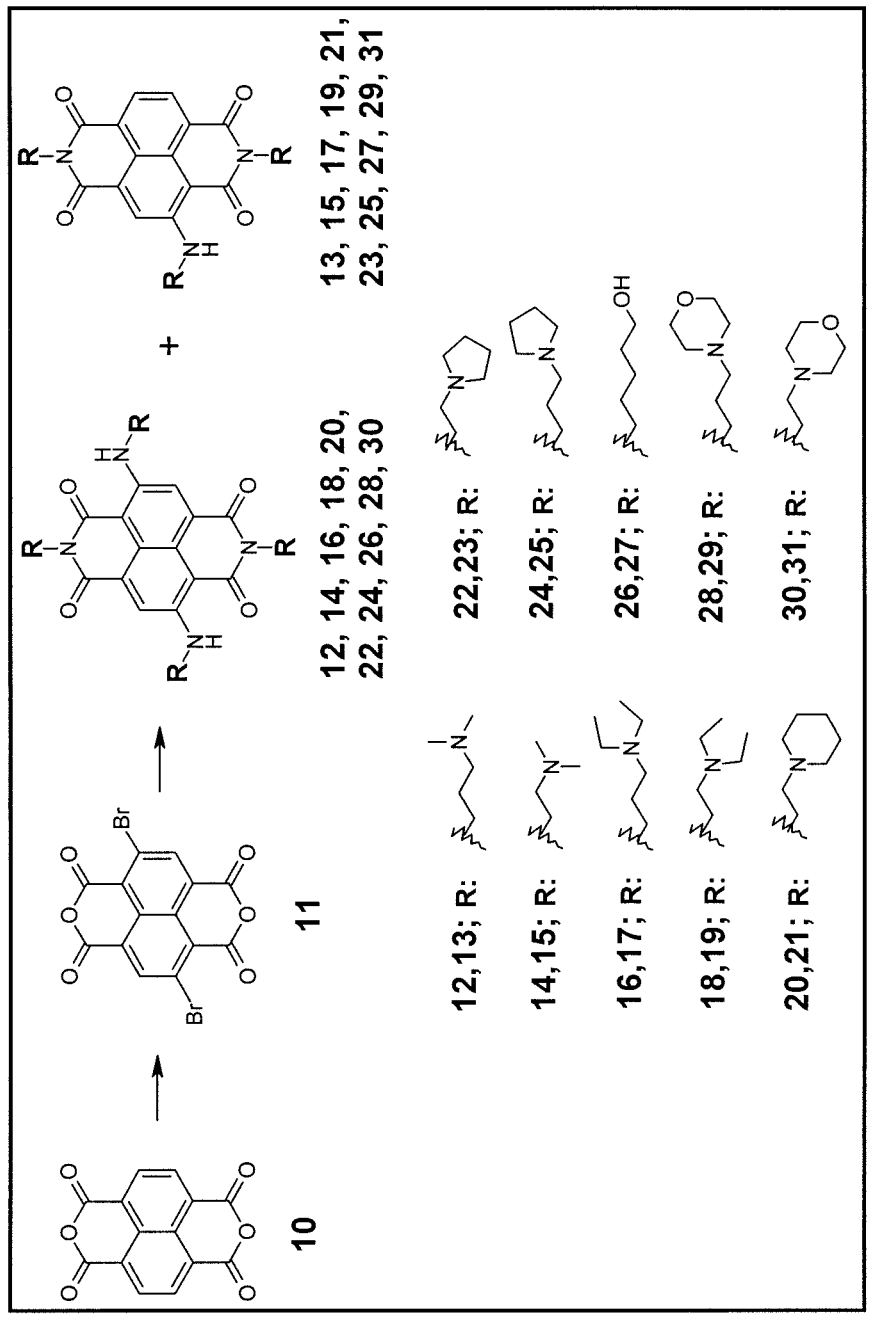
Figure 3:
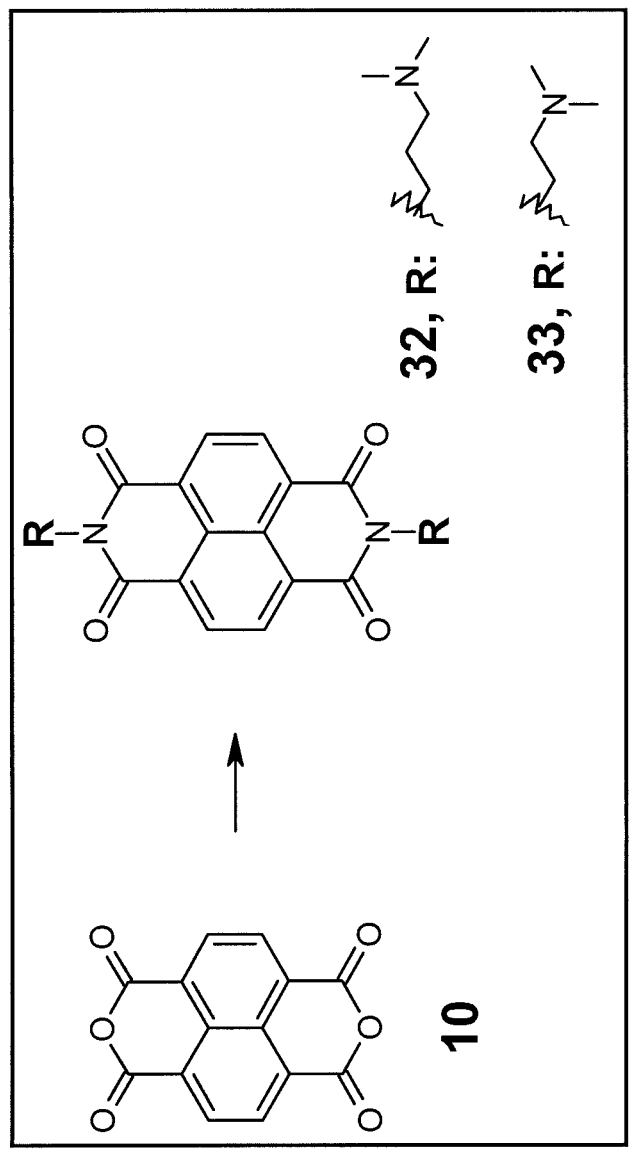
Figure 4:
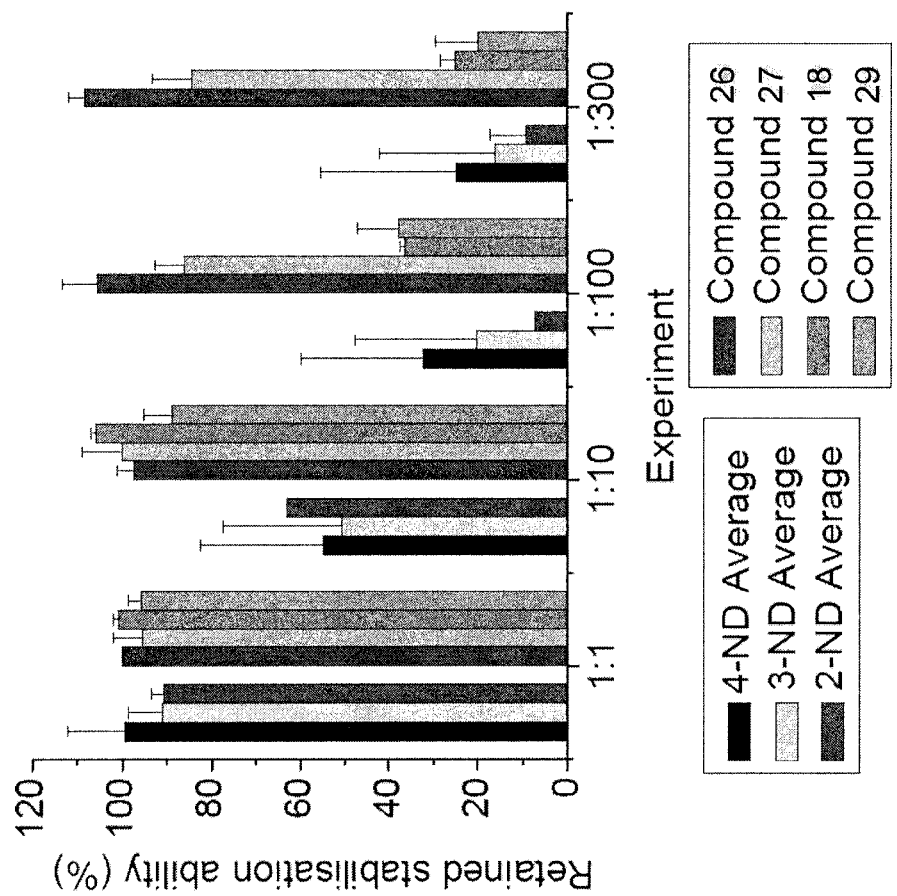
Figure 5:
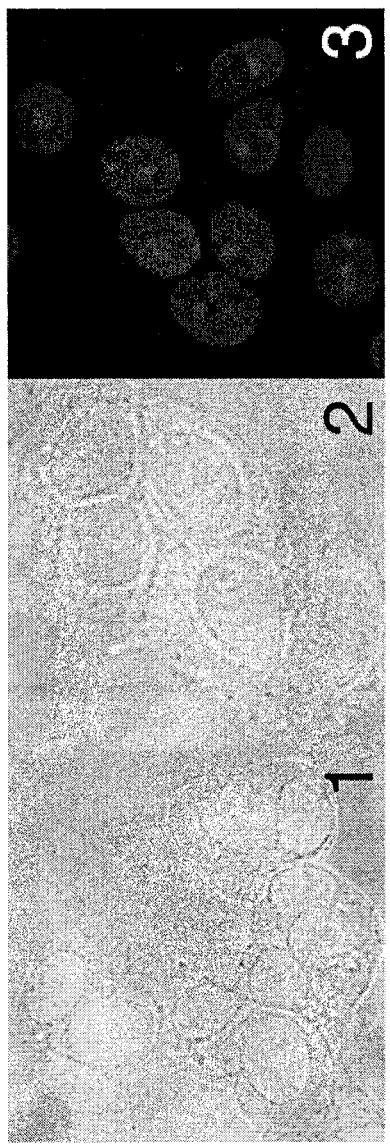

The invention will now be illustrated by the following Examples, and the accompanying figures, wherein
  FIG. 1 shows the synthetic route to compounds 8 and 9;
  FIG. 2 shows the synthetic route to compounds 12 to 31;
  FIG. 3 shows the synthetic route to compounds 32 and 33;
  FIG. 4 shows the competition FRET results; and
  FIG. 5 shows cell uptake detection under fluorescent confocal microscopy: (1)—Transmission/fluorescence composite image of compound 24 localised in the nucleus of MCF7 cells after 30 min exposure at 0.5 µM; (2)—Unspecific and low uptake of compound 30, 50 µM after 30 min; (3)—Compound 12 localisation in the nucleolus, 0.5 µM after 30 min.

EXPERIMENTAL

Example 1

General Methods

Reagents, solvents and chemicals were purchased from Sigma-Aldrich, Alfa Aesar, Lancaster Synthesis, GOSS or Avocado Organics and were used as supplied without further purification. All organic solvents were anhydrous. Microwave irradiation was performed with an Initiator microwave from Personal Chemistry. Reactions were monitored when possible using LC/MS (as described below). Work-up of an organic solution in the usual manner refers to stepwise drying with magnesium sulphate, filtration and then evaporation of the filtrate in vacuo.

HPLC analysis and purifications were performed using a Gilson system combining a 322 PUMP, a UV/VIS-155 detector (for preparative) or an Agilent 1100 SERIES detector (for analytical). The analytical column was C18 5µ (100×4.6 mm) (41622271(W), YMC, Japan). The preparative column was C18 5µ (100×20 mm) (201022272(W), YMC, Japan). Flows were 1 ml/min for analytical and 10 ml/min for preparative. Two analytical methods were used: method A (Aqueous solvent: 0.1% formic acid in water; Organic solvent: 0.1% formic acid in acetonitrile; Gradient: 100% aqueous for 5 minutes after injection, gradually to 75% aqueous over 17.5 minutes and gradually to 40% aqueous over 3 minutes) and method B (Aqueous solvent: 0.1% formic acid in water; Organic solvent: 0.1% formic acid in methanol; Gradient: 100% aqueous for 5 minutes after injection, gradually to 75% aqueous over 17.5 minutes and gradually to 40% aqueous over 3 minutes). Preparative HPLC were performed using method C (Aqueous solvent: 0.1% formic acid in water; Organic solvent: 0.1% formic acid in acetonitrile; Gradient: 10% aqueous for 5 minutes after injection, gradually to 60% aqueous over 25 minutes and gradually to 40% aqueous over 10 minutes). Compound isolation was achieved by fraction basification with ammonia followed by chloroform extraction and work up in the usual manner.

Melting points (mp) were recorded on a Stuart Scientific SMP1 melting point apparatus and are uncorrected. "mp d250" (e.g.) refers to decomposition observed at 250° C. NMR spectra were recorded at 400 MHz ($^1$H NMR) and 100 MHz ($^{13}$C NMR) on a Bruker spectrometer in CDCl$_3$, MeOD or DMSO-d$_5$ using the residual solvent peaks as internal standards. Coupling constant J values are given in hertz (Hz) designated as s (singlet), br s (broad singlet), d (doublet), t (triplet), dd (doublet of doublets), td (triple of doublets), tt (triplet of triplets), 4q (quartet), 5q (quintuplet) and m (multiplet). Signal assignments were done using 2D NMR (COSY) for $^1$H NMR data and $^{13}$C DEPT for the $^{13}$C NMR data. High resolution mass spectra (HRMS) and elemental analysis (CHN) services were provided by The School of Pharmacy. HRMS were conducted upon a Micromass Q-TTOF Ultima Global tandem mass spectrometer run under electrospray ionisation (ESI) or matrix assisted laser desorption/ionisation (MALDI) modes. CHN were conducted upon a Carlo Erba CHN1108 elemental analyser. LC/MS were performed using a Waters system combining a 2695 separation module, a Micromass ZQ spectrometer and a 2996 photodiode array detector (Mobile Phase: 50:50 (0.1% formic acid in water):(0.1% formic acid in acetonitrile); Run Time: 3 minutes isocratic; Mode: Electrospray positive (ES+); MS running conditions: 3 min run time; Cone: 25. Offset: 1; Skimmer: 1.5; RF lens: 0.1; Source Heater: 150 (degrees Celsius); Gas: 400 l/hr).

Synthetic Methods 1,3,4,5,6,8,9,10-octachloro-4,5,9,10-tetrahydropyrene (2)

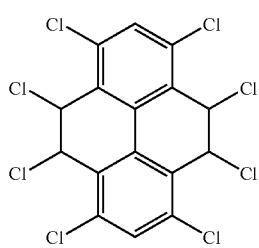

Pyrene (25 g, 124 mmol) and I$_2$ (0.75 g, 2.95 mmol) were dissolved in 1,2,4-trichlorobenzene (250 ml) in a 500 ml three-necked flask equipped with a mechanical stirrer. Chlorine gas was made bubble through the solution via a wide mouth glass cannula at the minimum flow. After 45 min at RT the temperature was raised to 50° C. and after another 45 min to 110° C. The mixture was stirred for 4 h then the heating and chlorine flow were stopped. The mixture was left to cool down at RT and then in an ice bath. The solid in the mixture was filtered, washed with toluene (2×50 ml) and dried under vacuum. A first crop (6.93 g) of the product was obtained as a pale green powder. The filtrate was left to stand at RT for 48 h. The solid formed was filtered and washed with toluene (2×50 ml) and dried to give a second crop of the desired product (5.28 g). Overall yield 2 (12.21 g, 25.3 mmol, 20.4%): mp 295-298° C.; $^1$H NMR (CDCl$_3$) δ: 5.81(s, 4H), 7.66(s, 2H); $^{13}$C NMR (CDCl$_3$) δ: 52.91(4×CH), 128.06(2×C), 128.65(4×C), 131.80(2×CH), 136.56(4×C); CHN: calcd C, 39.88%, H, 1.26%; found C, 39.69%, H, 1.08%; HRMS (ESI+) calcd C$_{16}$H$_6$Cl$_8$ [M+H]$^+$ 478.8056. Found: 478.8672.

1,3,4,6,8,9-hexachloropyrene (3) and
1,3,5,7,8,10-hexachloropyrene (4) regioisomers

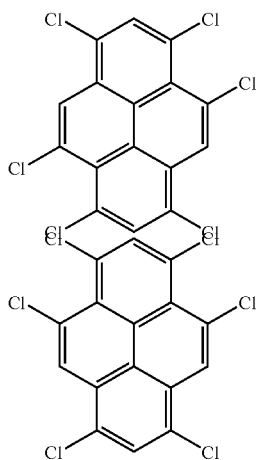

3

4

To a suspension of 2 (10.65 g, 22.1 mmol) in ethanol (85 ml) in a three-necked flask equipped with a mechanical stirrer, KOH (7.69 g, 137 mmol) was added slowly. The mixture was then heated at reflux for 5 h. The mixture was then left to cool down and it was filtered while still warm (50° C.). The solid obtained was washed with boiling water (2×20 ml) and ethanol (20 ml). The pale yellow solid was dried under air flow. Combined yield 3 and 4 (8.67 g, 21.2 mmol, 96%) as an isomeric mixture: mp>350° C.; CHN: calcd C, 47.00%, H, 0.99%; found C, 46.78%, H, 0.79%; HRMS (MALDI) calcd C$_{16}$H$_4$Cl$_6$ [M] 407.8415. Found: 407.7534.

2,5,7,10-tetrachloropyrene-3,8-quinone (5)

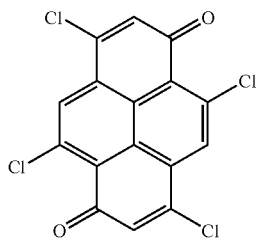

5

Fuming HNO$_3$ (12.7 ml) was added to a two-necked flask equipped with a thermometer in a −5° C. bath. The mixture of isomers 3 and 4 (4.33 g, 10.6 mmol) was added portionwise over a 30 min period with good stirring and maintaining the temperature under 5° C. After completion of the addition the mixture was stirred for another 15 min at 0° C. and then filtered to obtain a dark orange solid that was washed with acetic acid (5×10 ml) and water (2×10 ml). The product was purified by sublimation (1-2 mbar, 250° C.) to obtain an orange solid. Yield 5 (0.74 g, 2.0 mmol, 18.9%): mp 315-320° C.; $^1$H NMR (CDCl$_3$) δ: 7.06(s, 2H), 8.46(s, 2H); $^{13}$C NMR (CDCl$_3$) δ: 125.29(2×C), 127.45(2×C), 131.07(2×C), 131.27 (2×CH), 133.80(2×CH), 139.35(2×C), 144.36(2×C), 176.96 (2×C=O); CHN: calcd C, 51.94%, H, 1.09%; found C, 51.49%, H, 0.39%.

2,6-dichloro-1,4,5,8-naphthalenetetracarboxylic acid dianhydride (6)

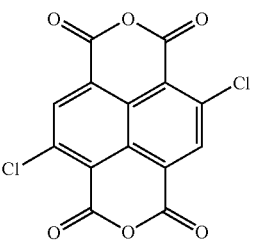

6

In a two-necked flask equipped with a condenser and a thermometer compound 5 (500 mg, 1.35 mmol) was dissolved in conc sulfuric acid (7 ml). The flask was heated at 100° C. and fuming nitric acid (0.775 ml) was added dropwise maintaining the temperature around 120° C. The mixture was then cooled down to 70° and poured onto ice (50 ml). The yellow solid formed was filtered and washed with cold acetic acid (5 ml). The product was purified by crystallisation from acetic acid. Yield 6 (157 mg, 0.47 mmol, 34.5%): mp>350° C.; $^1$H NMR (DMSO-d$_6$) δ: 8.69(s, 2H); $^{13}$C NMR (DMSO-d$_6$) δ: 121.47(2×C), 124.79(2×C), 128.86(2×C), 134.58(2× CH), 138.27(2×C), 159.90(2×C=O), 165.46(2×C=O); CHN: calcd C, 49.89%, H, 0.60%; found C, 49.46%, H, 0.38%.

N,N'-bis(3-(dimethylamino)propylamino)-2,6-
dichloro-1,4,5,8-naphthalenetetracarboxylic Acid
diimide (7)

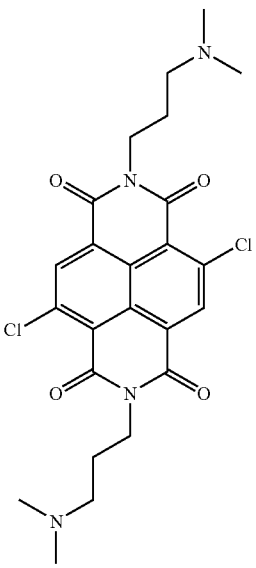

7

Compound 6 (50 mg, 0.150 mmol) was suspended with sonication in glacial acetic acid (1.5 ml) in a microwave reaction vessel. N,N-dimethyl-1,3-propanediamine (180 μL, 1.5 mmol, 10 eq) was added dropwise to the stirring mixture. The reaction tube was sealed and treated for 10 min at 120° C. in the microwave. The solution was then basified with 2M sodium carbonate in water and extracted with chloroform (3×5 ml). The organics were treated in the usual manner to afford a red solid. Yield 7 (61 mg, 0.121 mmol, 80.5%): $^1$H NMR (CDCl$_3$) δ: 1.91(5q, 4H, J=7.4 Hz), 2.22(s, 12H), 2.44 (t, 4H, J=7.0 Hz), 4.25(t, 4H, J=7.5 Hz), 8.76(s, 2H); $^{13}$C NMR (CDCl$_3$) δ: 25.54(2×CH$_2$), 39.74(2×CH$_2$), 45.18(4× CH$_3$), 57.07(2×CH$_2$), 122.32(2×C), 125.94(2×C), 127.08(2× C), 135.82(2×CH), 140.02(2×C), 160.50(2×C=O), 160.89 (2×C=O); HRMS (ES+) calcd C$_{24}$H$_{26}$Cl$_2$N$_4$O$_4$ [M+H]$^+$ 506.4016. Found: 506.4006.

N,N'-bis(3-(dimethylamino)propylamino)-2,6-bis(2-(piperidin-1yl)-ethylamino)-1,4,5,8-naphthalenetetracarboxylic acid diimide (8)

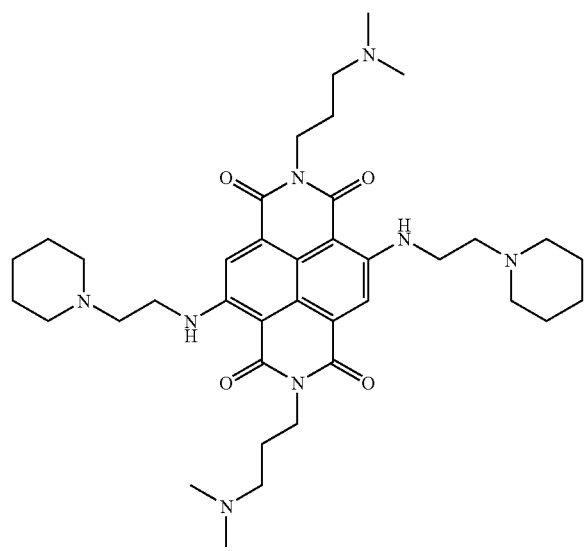

Compound 7 (45 mg, 0.089 mmol) was suspended in 1-(2-aminoethyl)piperidine (0.5 ml) in a microwave reaction vessel. The tube was flushed with nitrogen, sealed and treated at 150° C. for 10 min in the microwave. The amine was then evaporated off under high vacuum. The crude mixture was purified by HPLC to obtain 8 as a blue solid. Yield 8 (6.62 mg, 0.0096 mmol, 10.8%): $^1$H NMR (CDCl$_3$) δ: 1.47(m, 4H), 1.64(m, 8H), 1.90(5q, 4H, J=7.3 Hz), 2.26(s, 12H), 2.43(t, 4H, J=7.3 Hz), 2.51(m, 8H), 2.73(t, 4H, J=6.5 Hz), 3.58(m, 4H), 4.22(t, 4H, J=7.5 Hz), 8.07(s, 2H), 9.50(t, 2H, J=4.9 Hz); $^{13}$C NMR (CDCl$_3$) δ: 24.44(2×CH$_2$), 26.06(4×CH$_2$, 2×CH$_2$), 38.66(2×CH$_2$), 40.49(2×CH$_2$), 45.34(4×CH$_2$), 54.57(4×CH$_3$), 57.29(2×CH$_2$), 57.38(2×CH$_2$), 101.97(2×C), 118.38(2×CH), 121.07(2×C), 125.62(2×C), 148.90(2×C), 163.05(2×C=O), 165.79(2×C=O); HRMS (ES+) calcd C$_{38}$H$_{56}$N$_8$O$_4$ [M+2H]$^{2+}$ 345.2285. Found: 345.2293.

N,N'-bis(3-(dimethylamino)propylamino)-2,6-bis(3-hydroxypropylamino)-1,4,5,8-naphthalenetetracarboxylic acid diimide (9)

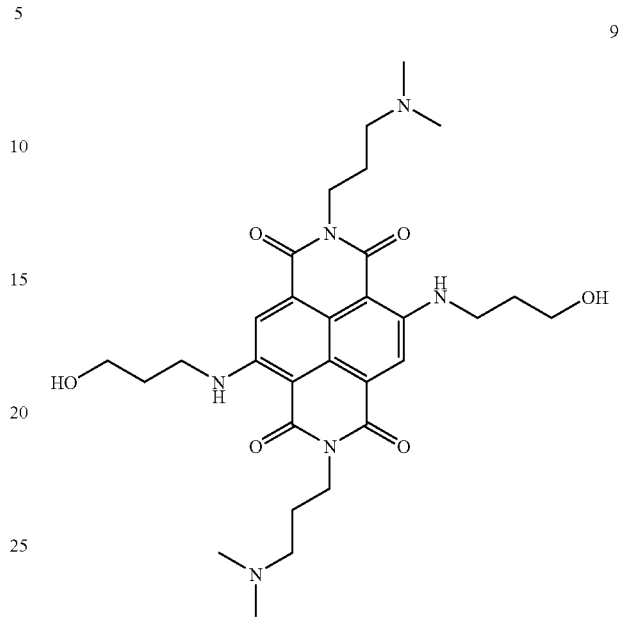

Compound 7 (45 mg, 0.089 mmol) was suspended in 3-amino-propanol (0.5 ml) in a microwave reaction vessel. The tube was flushed with nitrogen, sealed and treated at 150° C. for 10 min in the microwave. The mixture was then diluted down with water (25 ml), basified with 2M sodium carbonate and extracted with chloroform (5×5 ml). The organics were treated in the usual manner to afford a blue solid. The crude product was purified by HPLC to obtain 9 as a blue solid. Yield 9 (4.13 mg, 0.0071 mmol, 7.9%): $^1$H NMR (MeOD) δ: 1.98-2.07(m, 8H), 2.61(s, 12H), 2.84(m, 4H), 3.53(t, 4H, J=6.9 Hz), 3.84(t, 4H, J=6.0 Hz), 4.09(t, 4H, J=7.1 Hz), 7.68(s, 2H); $^{13}$C NMR (MeOD) δ: 25.98(2×CH$_2$), 33.15(2× CH$_2$), 39.15(2×CH$_2$), 41.29(2×CH$_2$), 44.71(4×CH$_3$), 57.66 (2×CH$_2$), 60.63(2×CH$_2$), 102.06(2×C), 118.41(2×CH), 121.52(2×C), 126.06(2×C), 146.49(2×C), 163.80(2×C=O), 166.72(2×C=O); HRMS (ES+) calcd C$_{30}$H$_{42}$N$_6$O$_6$ [M+H]$^+$ 583.3239. Found: 583.3260.

2,6-dibromo-1,4,5,8-naphthalenetetracarboxylic acid dianhydride (11)

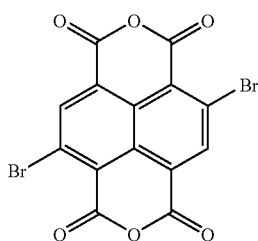

Naphthalene dianhydride (1 g, 3.72 mmol) was dissolved in fuming sulphuric acid (20% SO$_3$) (38 ml). A solution of dibromoisocyanuric acid (1.07 g, 3.72 mmol) in fuming sulphuric acid (18.5 ml) was added dropwise into it over a 4 h period. The mixture was stirred for a further 1 h and then poured onto ice (500 ml). The yellow solid that formed was filtered, washed with 0.5 M HCl in water (2×10 ml) and dried under vacuum. Yield 11 (1.30 g, 3.05 mmol, 82%): mp>350° C.; CHN: calcd C, 39.48%; H, 0.47%; found C, 39.50%; H, 0.47%.

N,N'-bis(3-(dimethylamino)propylamino)-2,6-bis(3-(dimethylamino) propylamino)-1,4,5,8-naphthalene-tetracarboxylic acid diimide (12) and N,N'-bis(3-(dimethylamino)propylamino)-2-(3-(dimethylamino)propylamino)-1,4,5,8-naphthalenetetracarboxylic acid diimide (13)

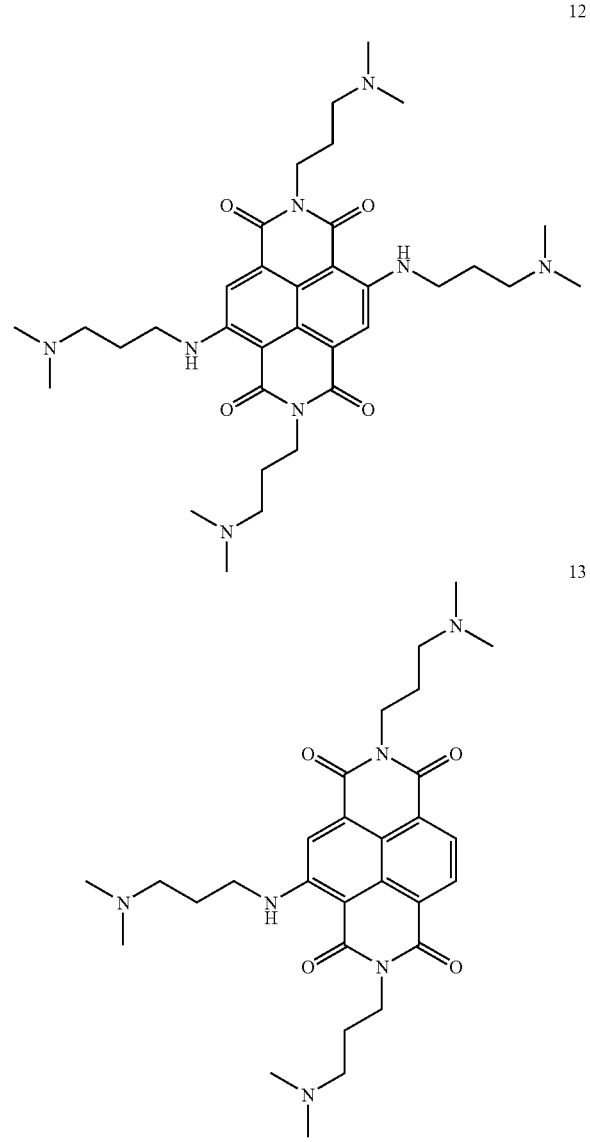

Compound 11 (100 mg, 0.234 mmol) was suspended in N,N-dimethyl-1,3-propanediamine (0.5 ml) in a microwave reaction vessel. The tube was flushed with nitrogen, sealed and treated at 150° C. for 10 min in the microwave. The amine was then evaporated off under high vacuum. The crude mixture was purified by HPLC to obtain 12 and 13 as a blue and an orange solid respectively. Yield 12 (23.1 mg, 0.036 mmol, 15.5%), 13 (12.6 mg, 0.024 mmol, 10.0%). 12: $^1$H NMR (CDCl$_3$) δ: 1.90(5q, 4H, J=7.4 Hz), 1.94(5q, 4H, J=7.0 Hz), 2.26(s, 12H), 2.27(s, 12H), 2.44(m, 8H), 3.57(m, 4H), 4.22 (m, 4H), 8.16(s, 2H), 9.41(t, 2H, J=5.1 Hz); $^{13}$C NMR (CDCl$_3$) δ: 26.10(2×CH$_2$), 27.51(2×CH$_2$), 38.71(2×CH$_2$), 41.25(2×CH$_2$), 45.41(4×CH$_3$), 45.52(4×CH$_3$), 56.99(2×CH$_2$), 57.32(2×CH$_2$), 101.93(2×C), 118.37(2×CH), 121.17(2×C), 125.79(2×C), 149.19(2×C), 163.05(2×C=O), 166.12(2×C=O); HRMS (ES+) calcd C$_{34}$H$_{52}$N$_8$O$_4$ [M+H]$^+$ 637.4190. Found: 637.4199. 13: $^1$H NMR (CDCl$_3$) δ: 1.90 (5q, 2H, J=7.2 Hz), 1.91(5q, 2H, J=7.5 Hz), 1.96(5q, 2H, J=6.9 Hz), 2.24(s, 6H), 2.26(s, 6H), 2.27(s, 6H), 2.41-2.47(m, 6H), 3.67(m, 2H), 4.23(m, 4H), 8.27(s, 1H), 8.32(d, 1H, J=7.8 Hz), 8.63(d, 1H, J=7.8 Hz), 10.21(t, 1H, J=5.5 Hz); $^{13}$C NMR (CDCl$_3$) δ: 26.00(CH$_2$), 26.08(CH$_2$), 27.48(CH$_2$), 38.68(CH$_2$), 39.25(CH$_2$), 41.32(CH$_2$), 45.36(2×CH$_3$), 45.41 (2×CH$_3$), 45.48(2×CH$_3$), 56.65(CH$_2$), 57.22(CH$_2$), 57.31(CH$_2$), 99.88(C), 119.42(C), 119.97(CH), 123.56(C), 124.36(CH), 126.18(C), 127.93(C), 129.57(C), 131.22(CH), 152.44(C), 162.99(C=O), 163.05(C=O), 163.39(C=O), 166.12(C=O); HRMS (ES+) calcd C$_{29}$H$_{40}$N$_6$O$_4$ [M+H]$^+$ 537.3189. Found: 537.3217.

N,N'-bis(2-(dimethylamino)ethylamino)-2,6-bis(2-(dimethylamino) ethylamino)-1,4,5,8-naphthalene-tetracarboxylic acid diimide (14) and N,N'-bis(3-(dimethylamino)ethylamino)-2-(3-(dimethylamino)ethylamino)-1,4,5,8-naphthalenetetracarboxylic acid diimide (15)

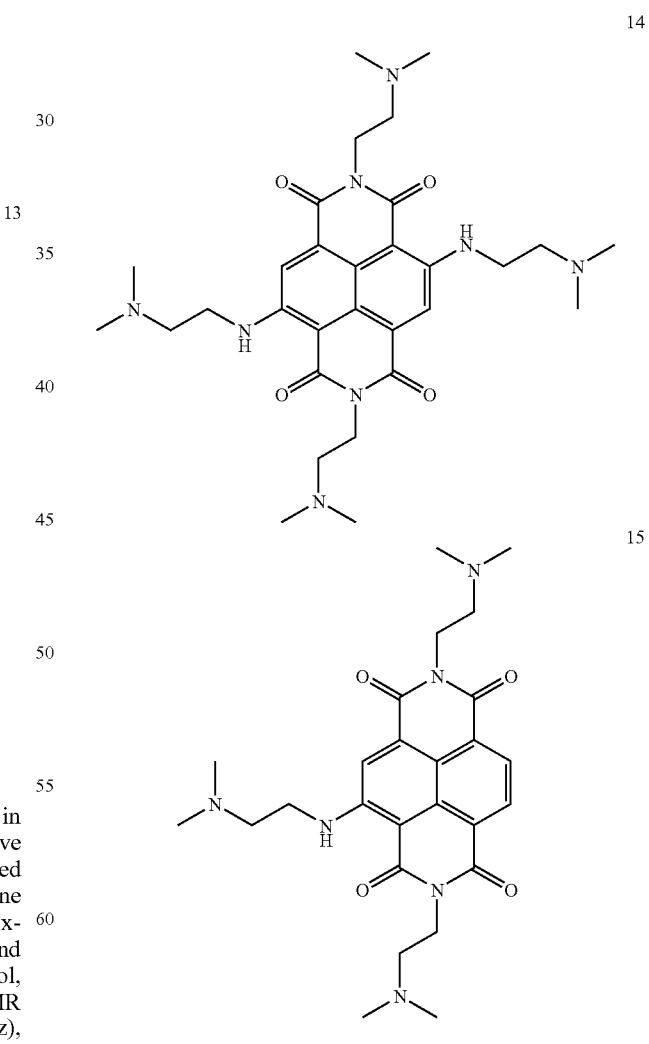

Compound 11 (100 mg, 0.234 mmol) was suspended in N,N-dimethyl-1,2-ethanediamine (0.6 ml) in a microwave reaction vessel. The tube was flushed with nitrogen, sealed and treated at 150° C. for 10 min in the microwave. The amine was then evaporated off under high vacuum. The crude mixture was purified by HPLC to obtain 14 and 15 as a blue and an orange solid respectively. Yield 14 (12.4 mg, 0.021 mmol, 9.1%), 15 (11.8 mg, 0.024 mmol, 10.2%). 14: $^1$H NMR (CDCl$_3$) δ: 2.36(s, 12H), 2.37(s, 12H), 2.63(t, 4H, J=7.1 Hz), 2.71(t, 4H, J=6.3 Hz), 3.56(m, 4H), 4.31(t, 4H, J=7.1 Hz), 8.06(s, 2H), 9.40(t, 2H, J=4.8 Hz); $^{13}$C NMR (CDCl$_3$) δ: 38.14(2×CH$_2$), 41.05(2×CH$_2$), 45.59(4×CH$_3$), 45.79(4×CH$_3$), 56.98(2×CH$_2$), 58.20(2×CH$_2$), 101.93(2×C), 118.29(2×CH), 121.12(2×0), 125.62(2×C), 148.91(2×C), 163.08(2×C=O), 165.84(2×C=O); HRMS (ES+) calcd C$_{30}$H$_{44}$N$_8$O$_4$ [M+H]$^+$ 581.3564. Found: 581.3558. 15: $^1$H NMR (CDCl$_3$) δ: 2.35(s, 6H), 2.37(s, 12H), 2.64-2.68(m, 4H), 2.73(t, 2H, J=6.3 Hz), 3.65(m, 2H), 4.31(t, 2H, J=6.8 Hz), 4.35(t, 2H, J=7.1 Hz), 8.20(s, 1H), 8.32(d, 1H, J=7.8 Hz), 8.63(d, 1H, J=7.8 Hz), 10.20(t, 1H, J=4.6 Hz); $^{13}$C NMR (CDCl$_3$) δ: 38.02(CH$_2$), 38.56(CH$_2$), 41.24(CH$_2$), 45.54(2× CH$_3$), 45.74(2×CH$_3$), 45.75(2×CH$_3$), 56.91(CH$_2$), 56.96(CH$_2$), 58.04(CH$_2$), 100.13(C), 120.08(C), 120.08(CH), 123.64(C), 124.50(CH), 126.14(C), 127.87(C), 129.61(C), 131.29(CH), 152.18(C), 163.12(C=O), 163.13 (C=O), 163.44(C=O), 165.95(C=O); HRMS (ES+) calcd C$_{26}$H$_{34}$N$_6$O$_4$ [M+H]$^+$ 495.2720. Found: 495.2705.

N,N'-bis(3-(diethylamino)propylamino)-2,6-bis(3-(diethylamino) propylamino)-1,4,5,8-naphthalenetetracarboxylic acid diimide (16) and N,N'-bis(3-(diethylamino)propylamino)-2-(3-(diethylamino) propylamino)-1,4,5,8-naphthalenetetracarboxylic acid diimide (17)

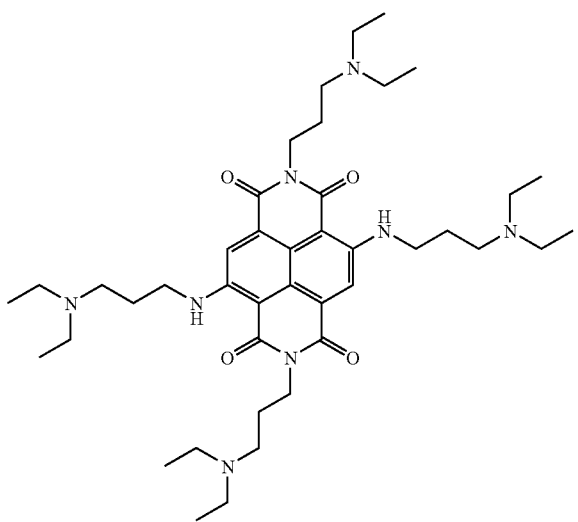

16

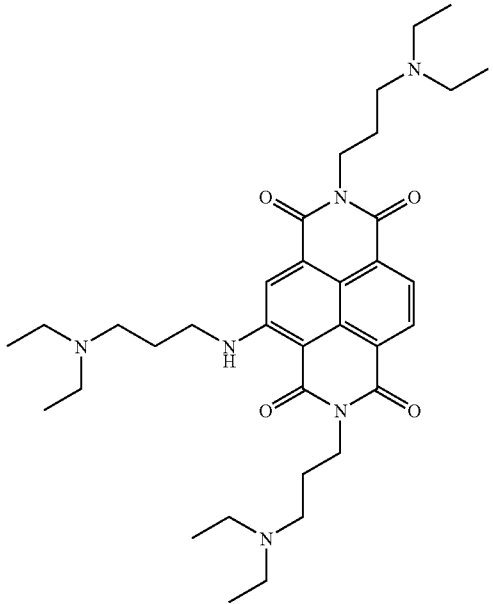

17

Compound 11 (100 mg, 0.234 mmol) was suspended in N,N-diethyl-1,3-ethanediamine (0.6 ml) in a microwave reaction vessel. The tube was flushed with nitrogen, sealed and treated at 150° C. for 10 min in the microwave. The amine was then evaporated off under high vacuum. The crude mixture was purified by HPLC to obtain 16 and 17 as a blue and an orange solid respectively. Yield 16 (29.3 mg, 0.039 mmol, 16.7%), 17 (20.0 mg, 0.032 mmol, 13.8%). 16: $^1$H NMR (CDCl$_3$) δ: 1.03(t, 12H, J=7.1 Hz), 1.04(t, 12H, J=7.1 Hz), 1.85-1.97(m, 8H), 2.53-2.63(m, 24H), 3.56(m, 4H), 4.20(t, 4H, J=7.6 Hz), 8.16(s, 2H), 9.42(t, 2H, J=5.3 Hz); $^{13}$C NMR (CDCl$_3$) δ: 11.69(4×CH$_3$, 4×CH$_3$), 25.28(2×CH$_2$), 27.14(2× CH$_2$), 38.98(2×CH$_2$), 41.45(2×CH$_2$), 46.72(4×CH$_2$), 46.89 (4×CH$_2$), 50.26(2×CH$_2$), 50.44(2×CH$_2$), 101.93(2×C), 118.38(2×CH), 125.35(2×C), 148.26(2×C), 149.20(2×C), 163.10(2×C=O), 166.11(2×C=O); HRMS (ES+) calcd C$_{42}$H$_{68}$N$_8$O$_4$ [M+H]$^+$ 749.5442. Found: 749.5436. 17: $^1$H NMR (CDCl$_3$) δ: 1.00-1.06(m, 18H), 1.86-1.98(m, 6H), 2.53-2.64(m, 18H), 3.65(m, 2H), 4.20(m, 4H), 8.23(s, 1H), 8.31(d, 1H, J=7.8 Hz), 8.63(d, 1H, J=7.8 Hz), 10.19(t, 1H, J=5.2 Hz); $^{13}$C NMR (CDCl$_3$) δ: 11.57(2×CH$_3$, 2×CH$_3$), 11.62(2×CH$_3$), 25.18(CH$_2$), 25.27(CH$_2$), 27.24(CH$_2$), 38.89 (CH$_2$), 39.48(CH$_2$), 41.54(CH$_2$), 46.64(2×CH$_2$), 46.68(2× CH$_2$), 46.84(2×CH$_2$), 50.03(CH$_2$), 50.38(CH$_2$), 50.39(CH$_2$), 99.82(C), 119.40(C), 119.93(CH), 123.55(C), 124.33(CH), 126.17(C), 127.91(C), 129.55(C), 131.20(CH), 152.37(C), 162.98(C=O), 163.03(C=O), 163.38(C=O), 166.06 (C=O); HRMS (ES+) calcd C$_{35}$H$_{52}$N$_6$O$_4$ [M+H]$^+$ 621.4128. Found: 621.4108.

N,N'-bis(3-(diethylamino)ethylamino)-2,6-bis(3-(diethylamino)ethylamino)-1,4,5,8-naphthalenetetracarboxylic acid diimide (18) and N,N'-bis(3-(diethylamino)ethylamino)-2-(3-(diethylamino)ethylamino)-1,4,5,8-naphthalenetetracarboxylic acid diimide (19)

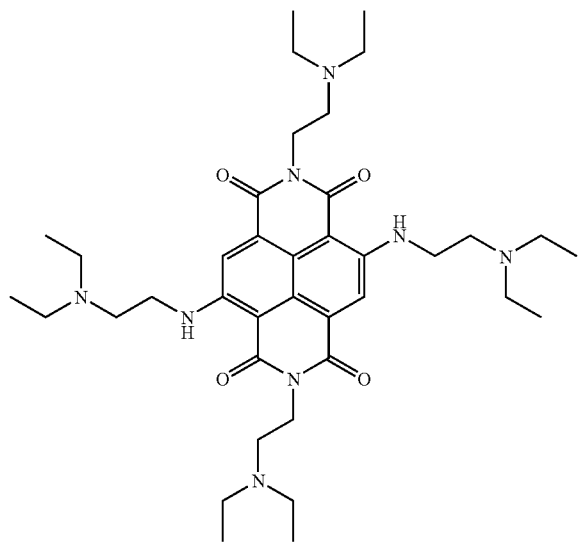

18

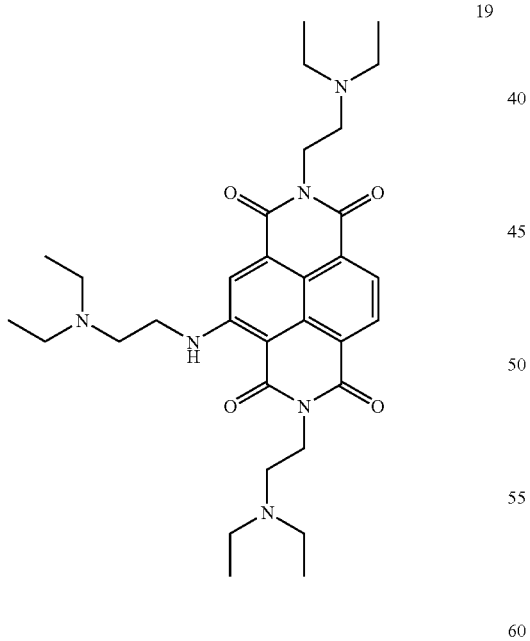

19

Compound 11 (100 mg, 0.234 mmol) was suspended in N,N-diethyl-1,2-ethanediamine (0.6 ml) in a microwave reaction vessel. The tube was flushed with nitrogen, sealed and treated at 150° C. for 10 min in the microwave. The amine was then evaporated off under high vacuum. The crude mixture was purified by HPLC to obtain 18 and 19 as a blue and an orange solid respectively. Yield 18 (22.2 mg, 0.032 mmol, 13.7%), 19 (26.6 mg, 0.046 mmol, 19.6%). 18: $^1$H NMR (CDCl$_3$) δ: 1.09(t, 24H, J=7.1 Hz), 2.61-2.69(m, 16H), 2.75 (m, 4H), 2.83(t, 4H, J=6.3 Hz), 3.51(m, 4H), 4.26(m, 4H), 8.05(s, 2H), 9.47(t, 2H, J=4.8 Hz); $^{13}$C NMR (CDCl$_3$) δ: 11.99(4×CH$_3$), 12.31(4×CH$_3$), 37.79(2×CH$_2$), 41.36(2×CH$_2$), 47.13(4×CH$_2$), 47.71(4×CH$_2$), 49.72(2×CH$_2$), 51.66(2×CH$_2$), 101.85(2×C), 118.33(2×CH), 121.04(2×C), 125.56(2×C), 148.87(2×C), 163.03(2×C=O), 165.65(2×C=O); HRMS (ES+) calcd C$_{38}$H$_{60}$N$_8$O$_4$ [M+H]$^+$ 693.4816. Found: 693.4813. 19: $^1$H NMR (CDCl$_3$) δ: 1.04-1.11(m, 18H), 2.61-2.69(m, 12H), 2.76(m, 4H), 2.84(t, 2H, J=6.2 Hz), 3.60(m, 2H), 4.23-4.31(m, 4H), 8.16(s, 1H), 8.27 (d, 1H, J=7.8 Hz), 8.58(d, 1H, J=7.8 Hz), 10.26(t, 1H, J=4.8 Hz); $^{13}$C NMR (CDCl$_3$) δ: 11.96(2×CH$_3$), 12.23(2×CH$_3$), 12.25(2×CH$_3$), 37.71(CH$_2$), 38.52(CH$_2$), 41.56(CH$_2$), 47.10 (2×CH$_2$), 447.58(2×CH$_2$), 47.66(2×CH$_2$), 49.67(CH$_2$), 49.85(CH$_2$), 51.63(CH$_2$), 99.88(C), 119.33(C), 120.26(CH), 123.52(C), 124.21(CH), 126.01(C), 127.63(C), 129.52(C), 131.04(CH), 152.09(C), 162.98(C=O), 163.01(C=O), 163.34(C=O), 165.66(C=O); HRMS (ES+) calcd C$_{32}$H$_{46}$N$_6$O$_4$ [M+H]$^+$ 579.3659. Found: 579.3616.

N,N'-bis(2-(piperidin-1-yl)ethylamino)-2,6-bis(2-(piperidin-1-yl)ethylamino)-1,4,5,8-naphthalenetetracarboxylic acid diimide (20) and N,N'-bis(2-(piperidin-1-yl)ethylamino)-2-(2-(piperidin-1-yl)ethylamino)-1,4,5,8-naphthalenetetracarboxylic acid diimide (21)

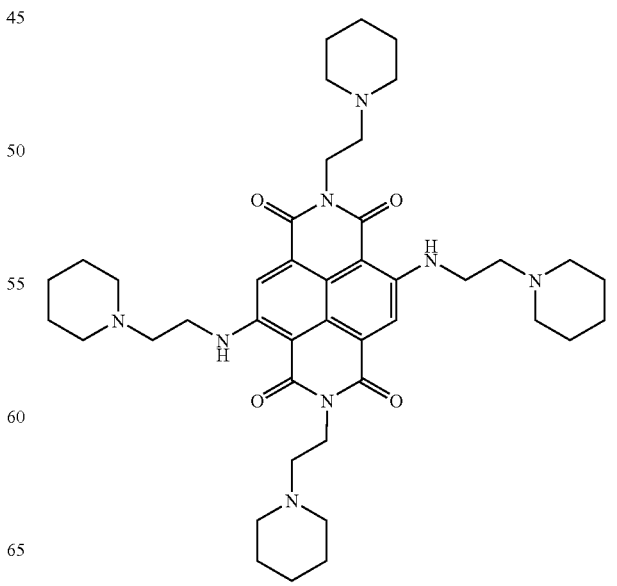

20

27

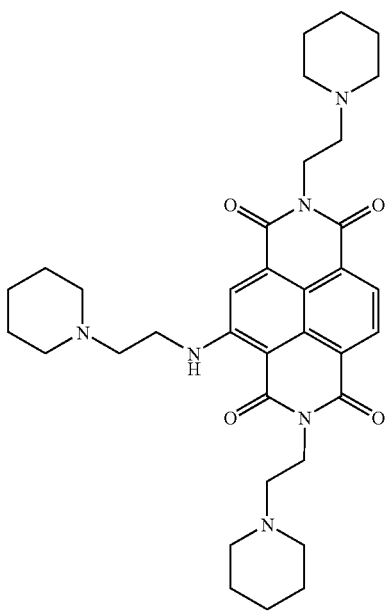

21

Compound 11 (100 mg, 0.234 mmol) was suspended in 1-(2-aminoethyl)piperidine (0.6 ml) in a microwave reaction vessel. The tube was flushed with nitrogen, sealed and treated at 150° C. for 10 min in the microwave. The amine was then evaporated off under high vacuum. The crude mixture was purified by HPLC to obtain 20 and 21 as a blue and an orange solid respectively. Yield 20 (19.3 mg, 0.026 mmol, 11.1%), 21 (20.9 mg, 0.034 mmol, 14.5%). 20: $^1$H NMR (CDCl$_3$) δ: 1.43-1.48(m, 8H), 1.56-1.65(m, 16H), 2.51(m, 8H), 2.56(m, 8H), 2.63(m, 4H), 2.72(t, 4H, J=6.5 Hz), 3.57(m, 4H), 4.33 (m, 4H), 8.07(s, 2H), 9.50(t, 2H, J=5.3 Hz); $^{13}$C NMR (CDCl$_3$) δ: 24.39(2×CH$_2$), 24.45(2×CH$_2$), 26.06(4×CH$_2$, 4×CH$_2$), 37.48(2×CH$_2$), 40.48(2×CH$_2$), 54.56(4×CH$_2$), 54.74(4×CH$_2$), 56.36(2×CH$_2$), 57.36(2×CH$_2$), 101.97(2×C), 118.38(2×CH), 121.10(2×C), 125.61(2×C), 148.89(2×C), 163.01(2×C=O), 165.71(2×C=O); HRMS (ES+) calcd C$_{42}$H$_{60}$N$_8$O$_4$ [M+H]$^+$ 741.4816. Found: 741.4855. 21: $^1$H NMR (CDCl$_3$) δ: 1.42-1.50(m, 6H), 1.53-1.59(m, 8H), 1.61-1.67(m, 4H), 2.52-2.56(m, 12H), 2.64(m, 4H), 2.74(t, 2H, J=6.4 Hz), 3.64(m, 2H), 4.30(t, 2H, J=7.2 Hz), 4.35(t, 2H, J=7.3 Hz), 8.16(s, 1H), 8.27(d, 1H, J=7.8 Hz), 8.58(d, 1H, J=7.8 Hz), 10.28(t, 1H, J=4.9 Hz); $^{13}$C NMR (CDCl$_3$) δ: 24.33(CH$_2$), 24.37(CH$_2$), 24.39(CH$_2$), 26.03(2×CH$_2$, 2×CH$_2$), 26.05(2×CH$_2$), 37.42(CH$_2$), 38.02(CH$_2$), 40.64(CH$_2$), 54.56(2×CH$_2$), 54.73(2×CH$_2$), 54.76(2×CH$_2$), 56.23(CH$_2$), 56.32(CH$_2$), 57.17(CH$_2$), 99.98(C), 119.36(C), 120.20(CH), 123.52(C), 124.24(CH), 126.03(C), 127.66(C), 129.52(C), 131.06(CH), 152.08(C), 162.93(C=O), 162.98 (C=O), 163.30(C=O), 165.70(C=O); HRMS (ES+) calcd C$_{35}$H$_{46}$N$_6$O$_4$ [M+H]$^+$ 615.3659. Found: 615.3669.

28

N,N'-bis(2-(pyrrolidin-1-yl)ethylamino)-2,6-bis(2-(pyrrolidin-1-yl)ethylamino)-1,4,5,8-naphthalenetetracarboxylic acid diimide (22) and N,N'-bis(2-(pyrrolidin-1-yl)ethylamino)-2-(2-(pyrrolidin-1-yl) ethylamino)-1,4,5,8-naphthalenetetracarboxylic acid diimide (23)

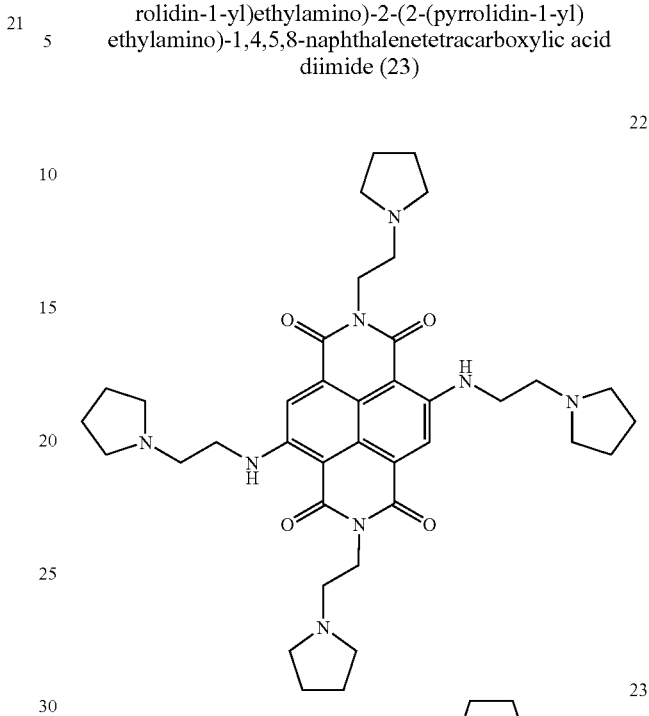

22

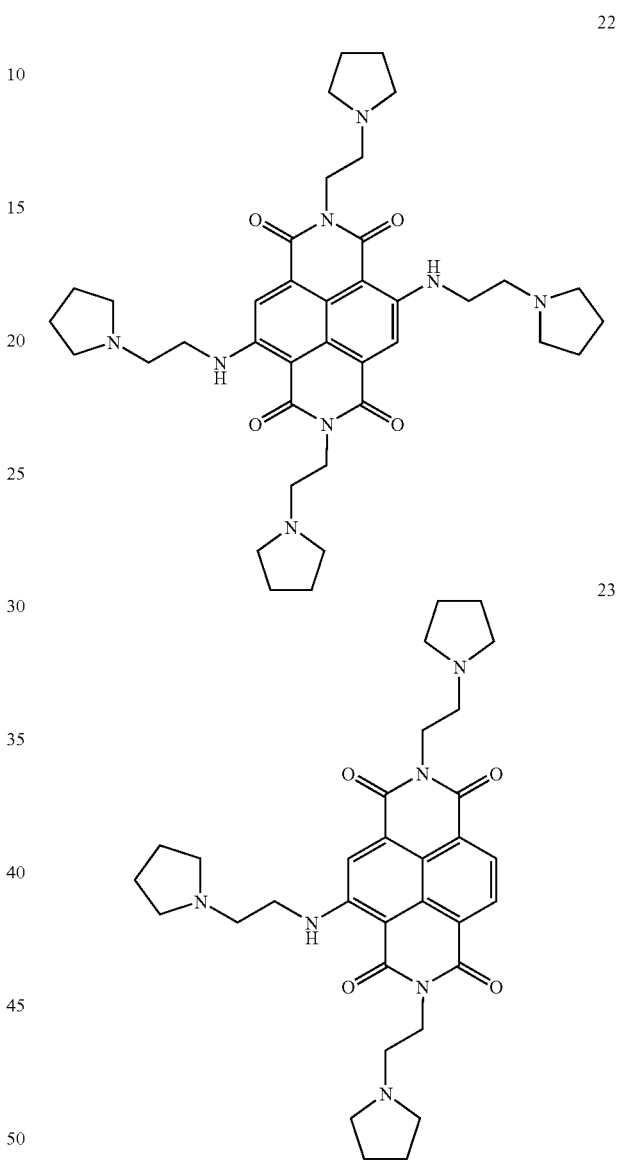

23

Compound 11 (100 mg, 0.234 mmol) was suspended in 1-(2-aminoethyl)pyrrolidine (0.6 ml) in a microwave reaction vessel. The tube was flushed with nitrogen, sealed and treated at 150° C. for 10 min in the microwave. The amine was then evaporated off under high vacuum. The crude mixture was purified by HPLC to obtain 22 and 23 as a blue and an orange solid respectively. Yield 22 (34.1 mg, 0.050 mmol, 21.3%), 23 (37.2 mg, 0.065 mmol, 27.7%). 22: $^1$H NMR (CDCl$_3$) δ: 1.76-1.84(m, 16H), 2.62-2.66(m, 16H), 2.77(t, 4H, J=7.3 Hz), 2.87(t, 4H, J=6.6 Hz), 3.59(m, 4H), 4.32(t, 4H, J=7.4 Hz), 8.05(s, 2H), 9.44(t, 2H, J=5.1 Hz); $^{13}$C NMR (CDCl$_3$) δ: 23.59(4×CH$_2$), 23.63(4×CH$_2$), 39.12(2×CH$_2$), 42.28(2×CH$_2$), 53.61(2×CH$_2$), 54.23(4×CH$_2$), 54.33(4×CH$_2$), 54.90(2×CH$_2$), 101.88(2×0), 118.22(2×CH), 121.05(2×0), 125.58(2×C), 148.91(2×C), 162.92(2×C=O), 165.77(2×C=O); HRMS (ES+) calcd C$_{38}$H$_{52}$N$_8$O$_4$ [M+H]$^+$ 685.4190. Found: 685.4207. 23 $^1$H NMR (CDCl$_3$) δ: 1.78-1.84(m, 12H), 2.65-2.68(m, 12H), 2.81(m, 4H), 2.90(t, 2H, J=6.5 Hz), 3.67(m, 4H), 4.29-4.36(m, 4H), 8.13(s, 1H), 8.24 (d, 1H, J=7.8 Hz), 8.54(d, 1H, J=7.8 Hz), 10.20(t, 1H, J=5.0 Hz); $^{13}$C NMR (CDCl$_3$) δ: 23.59(2×CH$_2$, 2×CH$_2$), 23.66(2× CH$_2$), 38.94(CH$_2$), 39.52(CH$_2$), 42.41(CH$_2$), 53.52(CH$_2$, CH$_2$), 54.19(2×CH$_2$), 54.30(2×CH$_2$), 54.34(2×CH$_2$), 54.70 (CH$_2$), 99.90(C), 119.31(C), 119.95(CH), 123.44(C), 124.29 (CH), 126.00(C), 127.69(C), 129.42(C), 131.07(CH), 152.10 (C), 162.86(C=O), 162.90(C=O), 163.22(C=O), 165.75 (C=O); HRMS (ES+) calcd C$_{32}$H$_{40}$N$_6$O$_4$ [M+H]$^+$ 573.3189. Found: 573.3185.

N,N'-bis(3-(pyrrolidin-1-yl)propylamino)-2,6-bis(3-(pyrrolidin-1-yl)propylamino)-1,4,5,8-naphthalene-tetracarboxylic acid diimide (24) and N,N'-bis(3-(pyrrolidin-1-yl)propylamino)-2-(3-(pyrrolidin-1-yl)propylamino)-1,4,5,8-naphthalenetetracarboxylic acid diimide (25)

24

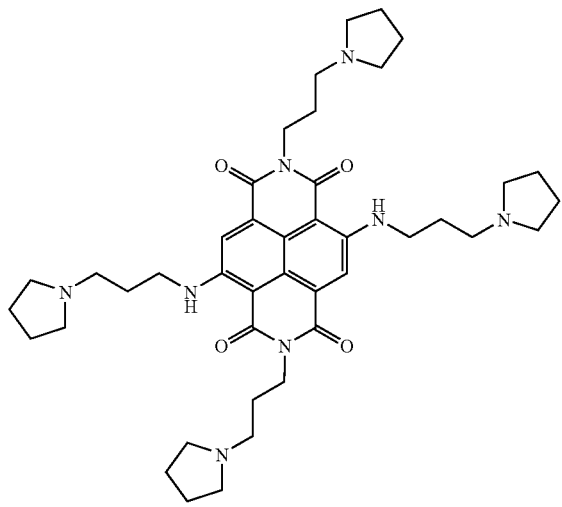

25

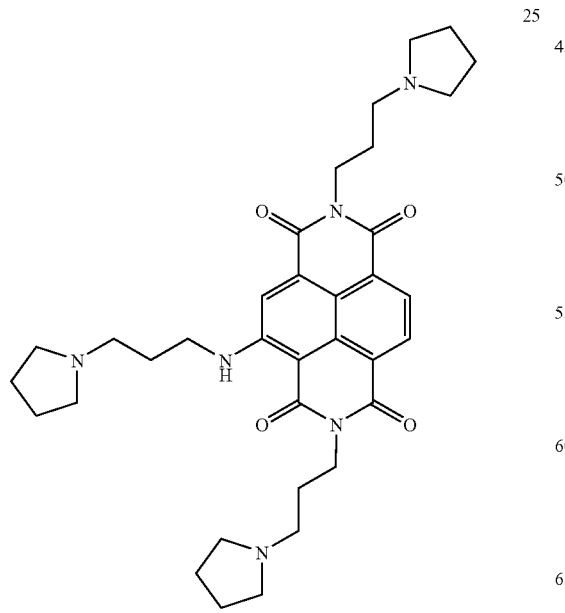

Compound 11 (50 mg, 0.117 mmol) was suspended in 1-(3-aminopropyl)pyrrolidine (0.2 ml) in a microwave reaction vessel. The tube was flushed with nitrogen, sealed and treated at 150° C. for 10 min in the microwave. The amine was then evaporated off under high vacuum. The crude mixture was purified by HPLC to obtain 24 and 25 as a blue and an orange solid respectively. Yield 24(13.2 mg, 0.018 mmol, 15.2%), 25(14.6 mg, 0.024 mmol, 20.3%). 24: $^1$H NMR (CDCl$_3$) δ: 1.74(m, 8H), 1.81(m, 8H), 1.92-2.03(m, 8H), 2.53(m, 16H), 2.60(t, 4H, J=7.4 Hz), 2.63(t, 4H, J=7.1 Hz), 3.59(m, 4H), 4.26(t, 4H, J=7.4 Hz), 8.19(s, 2H), 9.44(t, 2H, J=5.4 Hz); $^{13}$C NMR (CDCl$_3$) δ: 23.42(4×CH$_2$), 23.49(4× CH$_2$), 26.71(2×CH$_2$), 28.39(2×CH$_2$), 38.54(2×CH$_2$), 41.43 (2×CH$_2$), 53.58(2×CH$_2$), 53.67(2×CH$_2$), 53.71(4×CH$_2$), 54.06(4×CH$_2$), 101.88(2×C), 118.46(2×CH), 121.29(2×C), 125.65(2×C), 149.17(2×C), 163.00(2×C=O), 166.17(2× C=O); HRMS (ES+) calcd C$_{42}$H$_{60}$N$_8$O$_4$ [M+H]$^+$ 741.4816. Found: 741.4779. 25: $^1$H NMR (CDCl$_3$) δ: 1.70(m, 4H), 1.75(m, 4H), 1.82(m, 4H), 1.93-2.04(m, 6H), 2.55(m, 12H), 2.59-2.65(m, 6H), 3.69(m, 2H), 4.27(m, 4H), 8.29(s, 1H), 8.33(d, 1H, J=7.8 Hz), 8.64(d, 1H, J=7.8 Hz), 10.22(t, 1H, J=5.4 Hz); $^{13}$C NMR (CDCl$_3$) δ: 23.46(2×CH$_2$), 23.48(2× CH$_2$), 23.56(2×CH$_2$), 27.17(CH$_2$), 27.31(CH$_2$), 28.78(CH$_2$), 38.84(CH$_2$), 39.40(CH$_2$), 41.63(CH$_2$), 53.52(CH$_2$), 53.92(CH$_2$), 54.00(CH$_2$), 54.02(2×CH$_2$), 54.07(2×CH$_2$), 54.25(2×CH$_2$), 99.86(C), 119.43(C), 120.00(CH), 123.56(C), 124.31(CH), 126.23(C), 127.94(C), 129.56(C), 131.20(CH), 152.47(C), 163.04(C=O), 163.12(C=O), 163.45(C=O), 166.13(C=O); HRMS (ES+) calcd C$_{35}$H$_{46}$N$_6$O$_4$ [M+H]$^+$ 615.3659. Found: 615.3663.

N,N'-bis(5-hydroxypentanamino)-2,6-bis(5-hydroxy-pentanamino)-1,4,5,8-naphthalenetetracarboxylic acid diimide (26) and N,N'-bis(5-hydroxypentan-amino)-2-(5-hydroxypentanamino)-1,4,5,8-naphtha-lenetetracarboxylic acid diimide (27)

26

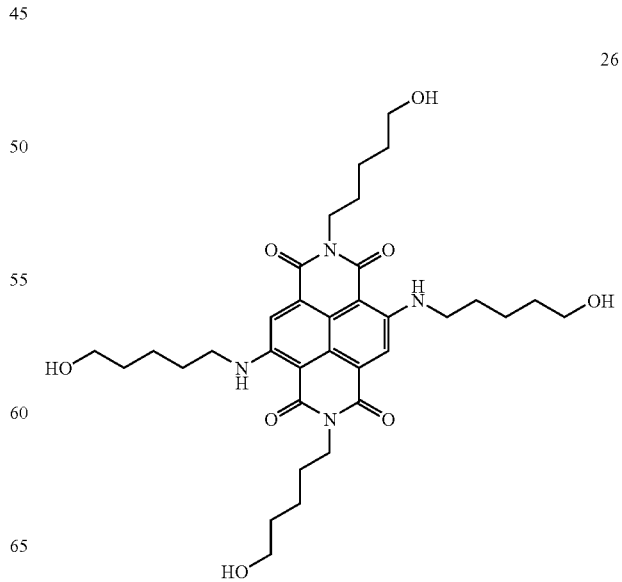

31

-continued

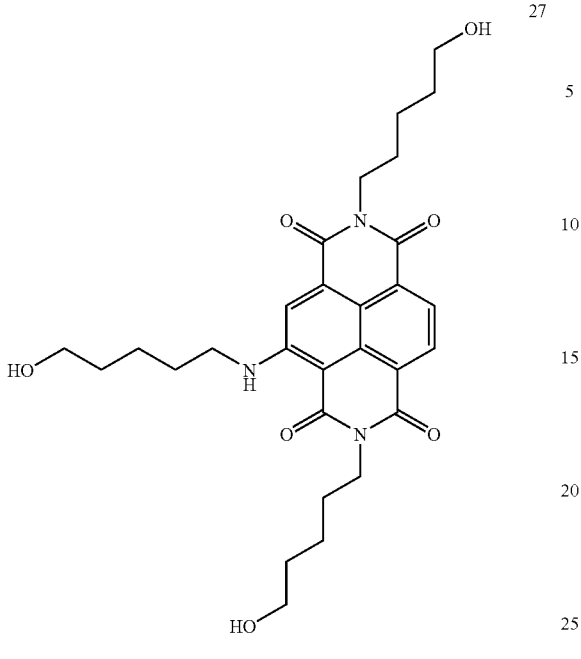

27

Compound 11 (50 mg, 0.117 mmol) was suspended in 5-amino-1-pentanol (0.5 ml) in a microwave reaction vessel. The tube was flushed with nitrogen, sealed and treated at 150° C. for 10 min in the microwave. The mixture was then diluted down with water (100 ml). The mixture was left at RT for 24 hours. The sticky solid formed was taken by filtration, dissolved in DMF (5 ml) and evaporated under high vacuum. The crude mixture was purified by HPLC to obtain 26 and 27 as a blue and an orange solid respectively. Yield 26 (3.8 mg, 0.006 mmol, 5.1%), 27 (3.25 mg, 0.006 mmol 5.1%). 26 $^1$H NMR (DMSO-$d_6$) δ: 1.36(m, 4H), 1.45-1.62(m, 16H), 1.73 (5q, 4H, J=6.9 Hz), 3.36(m, 4H), 3.41(4q, 4H, J=5.2 Hz), 3.47(4q, 4H, J=5.3 Hz), 3.90(m, 4H), 4.36(t, 2H, J=5.1 Hz), 4.42(t, 2H, J=5.1 Hz), 7.63(s, 2H), 9.07(t, 2H, J=5.0 Hz); $^{13}$C NMR (DMSO-$d_6$) δ: 23.03(2×$CH_2$), 23.09(2×$CH_2$), 27.16 (2×$CH_2$), 28.53(2×$CH_2$), 32.10(2×$CH_2$), 32.11(2×$CH_2$), 40.24(2×$CH_2$), 42.24(2×$CH_2$), 60.40(2×$CH_2$), 60.50(2×$CH_2$), 100.27(2×0), 119.71(2×CH), 147.83(2×C), 155.42(2×C), 155.44(2×C), 161.45(2×C=O), 164.91(2× C=O); HRMS (ES+) calcd $C_{34}H_{48}N_4O_8$ [M+H]$^+$ 641.3550. Found: 641.3563. 27: $^1$H NMR (DMSO-$d_6$) δ: 1.37(m, 4H), 1.47(m, 8H), 1.63(m, 4H), 1.73(5q, 2H, J=6.9 Hz), 3.38-3.42 (m, 4H), 3.45(4q, 2H, J=5.3 Hz), 3.55(4q, 2H, J=6.5 Hz), 3.98(m, 4H), 4.35(t, 1H, J=5.1 Hz), 4.35(t, 1H, J=5.1 Hz), 4.41(t, 1H, J=5.1 Hz), 7.93(s, 1H), 8.09(d, 1H, J=7.8 Hz), 8.38(d, 1H, J=7.8 Hz), 9.94(t, 1H, J=5.4 Hz); $^{13}$C NMR (DMSO-$d_6$) δ: 23.04($CH_2$, $CH_2$), 23.12($CH_2$), 27.26($CH_2$), 27.29($CH_2$), 28.75($CH_2$), 32.10($CH_2$), 32.18($CH_2$), 32.20($CH_2$), 41.77($CH_2$), 41.84($CH_2$), 42.46($CH_2$), 60.46($CH_2$), 60.48($CH_2$), 60.55($CH_2$), 98.38(C), 119.14(CH), 121.26(C), 122.41(C), 122.82(C), 123.53(CH), 128.57(C), 130.43(C), 130.48(CH), 141.29(C), 162.09 (C=O), 162.63(C=O), 165.19(C=O), 165.43(C=O); HRMS (ES+) calcd $C_{29}H_{37}N_3O_7$ [M+H]$^+$ 540.2710. Found: 540.2715.

32

N,N'-bis(3-(morpholino-4-yl)propylamino)-2,6-bis (3-(morpholino-4-yl)propylamino)-1,4,5,8-naphthalenetetracarboxylic Acid diimide (28) and N,N'-bis (3-(morpholino-4-yl)propylamino)-2-(3-(morpholino-4-yl)propylamino)-1,4,5,8-naphthalenetetracarboxylic Acid diimide (29)

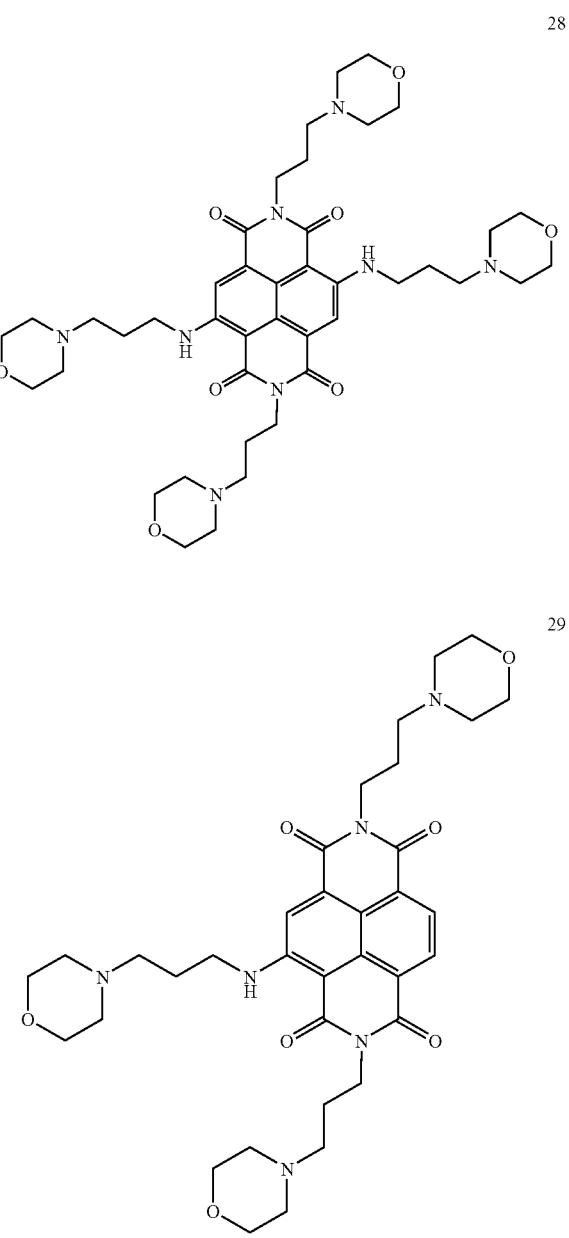

Compound 11 (25 mg, 0.058 mmol) was suspended in 3-morpholino-1-propylamine (2 ml) in a microwave reaction vessel. The tube was flushed with nitrogen, sealed and treated at 150° C. for 10 min in the microwave. The mixture was then diluted down with water (50 ml) and extracted with chloroform (5×10 ml). The organics were treated in the usual manner to afford a dark brown solid. The crude mixture was purified by HPLC to obtain 28 and 29 as a blue and an orange solid respectively. Yield 28 (4.97 mg, 0.006 mmol, 10.5%), 29 (3.19 mg, 0.005 mmol, 8.2%). 28: $^1$H NMR (CDCl$_3$) δ: 1.89-1.99(m, 8H), 2.44-2.53(m, 24H), 3.59(m, 4H), 3.62(m, 8H), 3.75(m, 8H), 4.25(t, 4H, J=7.3 Hz), 8.16(s, 2H), 9.43(t, 2H, J=5.4 Hz); $^{13}$C NMR (CDCl$_3$) δ: 24.68(2×CH$_2$), 26.31(2×CH$_2$), 38.82(2×CH$_2$), 41.32(2×CH$_2$), 53.57(2×CH$_2$), 53.84 (2×CH$_2$), 56.26(4×CH$_2$), 56.53(4×CH$_2$), 66.91(4×CH$_2$), 66.96(4×CH$_2$), 101.98(2×C), 118.32(2×CH), 121.19(2×C), 125.84(2×C), 149.18(2×C), 163.10(2×C=O), 166.17(2×C=O); HRMS (ES+) calcd C$_{42}$H$_{60}$N$_8$O$_8$ [M+H]$^+$ 805.4607. Found: 805.4608. 29: $^1$H NMR (CDCl$_3$) δ: 1.92-1.96(m, 6H), 2.43-2.54(m, 18H), 3.56(t, 4H, J=4.5 Hz), 3.62(t, 4H, J=4.5 Hz), 3.70(m, 2H), 3.76(m, 4H), 4.27(m, 4H), 8.27(s, 1H), 8.34(d, 1H, J=7.8 Hz), 8.65(d, 1H, J=7.8 Hz), 10.21(t, 1H, J=5.7 Hz); $^{13}$C NMR (CDCl$_3$) δ: 24.42(CH$_2$), 24.44(CH$_2$), 26.31(CH$_2$), 38.79(CH$_2$), 39.35(CH$_2$), 41.34(CH$_2$), 53.56(2×CH$_2$, 2×CH$_2$), 53.83(2×CH$_2$), 55.94(CH$_2$), 56.45(CH$_2$), 56.53(CH$_2$), 66.87(2×CH$_2$), 66.92(2×CH$_2$), 66.95(2×CH$_2$), 98.84(C), 116.27(C), 119.82(CH), 123.65(C), 124.45(CH), 126.28(C), 127.20(C), 129.61(C), 132.75(CH), 151.51(C), 163.09(C=O), 163.42(C=O), 166.24(C=O), 166.76(C=O); HRMS (ES+) calcd C$_{35}$H$_{46}$N$_6$O$_7$ [M+H]$^+$ 663.3501. Found: 663.3524.

N,N'-bis(2-(morpholino-4-yl)ethylamino)-2,6-bis(2-(morpholino-4-yl)ethylamino)-1,4,5,8-naphthalenetetracarboxylic acid diimide (30) and N,N'-bis(2-(morpholino-4-yl)ethylamino)-2-(2-(morpholino-4-yl)ethylamino)-1,4,5,8-naphthalenetetracarboxylic Acid diimide (31)

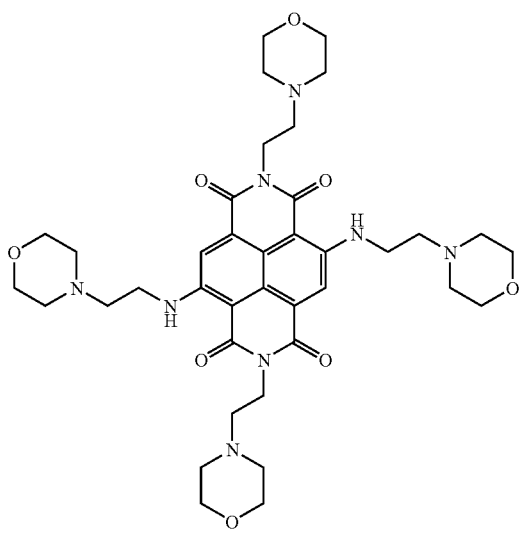

30

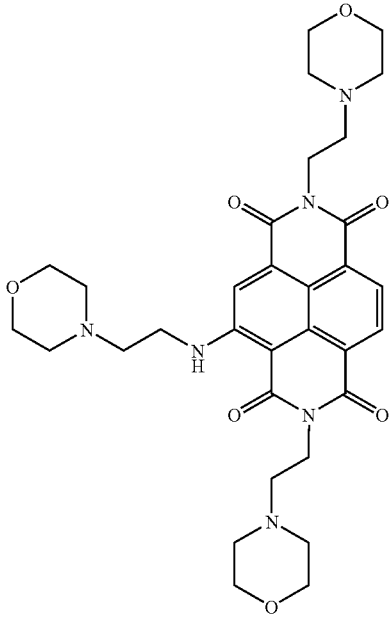

31

Compound 11 (25 mg, 0.058 mmol) was suspended in 2-morpholino-1-ethylamine (2 ml) in a microwave reaction vessel. The tube was flushed with nitrogen, sealed and treated at 150° C. for 10 min in the microwave. The mixture was then diluted down with water (50 ml) and extracted with chloroform (5×10 ml). The organics were treated in the usual manner to afford a dark brown solid. The crude mixture was purified by HPLC to obtain 30 and 31 as a blue and an orange solid respectively. Yield 30 (2.74 mg, 0.004 mmol, 6.3%), 31 (2.48 mg, 0.004 mmol, 6.8%). 30: $^1$H NMR (CDCl$_3$) δ: 2.57-2.61(m, 16H), 2.70(t, 4H, J=6.9 Hz), 2.78(t, 4H, J=6.2 Hz), 3.61(m, 4H), 3.69(m, 8H), 3.77(m, 8H), 4.35(t, 4H, J=6.9 Hz), 8.14(s, 2H), 9.58(t, 2H, J=4.9 Hz); $^{13}$C NMR (CDCl$_3$) δ: 37.14(2×CH$_2$), 39.99(2×CH$_2$), 53.49(4×CH$_2$), 53.84(4×CH$_2$), 56.15(2×CH$_2$), 56.93(2×CH$_2$), 67.04(4×CH$_2$, 4×CH$_2$), 102.17(2×0), 118.59(2×CH), 121.33(2×0), 130.00(2×0), 148.95(2×0), 163.09(2×C=O), 165.88(2×C=O); HRMS (ES+) calcd C$_{38}$H$_{52}$N$_8$O$_8$ [M+2H]$^{2+}$ 375.2027. Found: 375.2008. 31: $^1$H NMR (CDCl$_3$) δ: 2.60(m, 12H), 2.70(m, 4H), 2.81(t, 2H, J=6.2 Hz), 3.65-3.70(m, 10H), 3.78(m, 4H), 4.33(t, 2H, J=6.7 Hz), 4.38(t, 2H, J=6.9 Hz), 8.23(s, 1H), 8.35(d, 1H, J=7.8 Hz), 8.66(d, 1H, J=7.8 Hz), 10.35(t, 1H, J=4.9 Hz); $^{13}$C NMR (CDCl$_3$) δ: 37.11(CH$_2$), 37.64(CH$_2$), 40.13(CH$_2$), 53.48(2×CH$_2$), 53.84(2×CH$_2$, 2×CH$_2$), 56.05(CH$_2$), 56.14(CH$_2$), 56.82(CH$_2$), 67.01(2×CH$_2$), 67.03(2×CH$_2$), 67.05(2×CH$_2$), 104.37(C), 114.032(C), 120.20(CH), 123.69(C), 124.59(CH), 126.12(C), 127.25(C), 129.12(C), 131.31(CH), 149.11(C), 163.05(C=O), 163.39(C=O), 164.52(C=O), 165.91(C=O); HRMS (ES+) calcd C$_{32}$H$_{40}$N$_6$O$_7$ [M+H]$^+$ 621.3031. Found: 621.3049.

N,N'-bis(3-(dimethylamino)propylamino)-1,4,5,8-naphthalenetetracarboxylic acid diimide (32) (Prior Art)

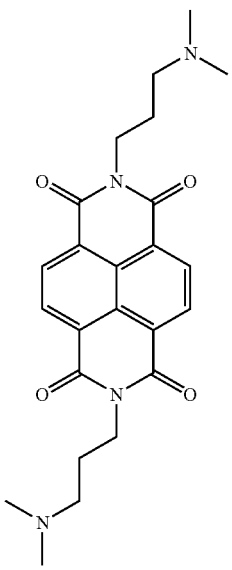

Naphthalene dianhydride (100 mg, 0.373 mmol) was suspended in N,N-dimethyl-1,3-propanediamine (2 ml) in a microwave reaction vessel. The tube was flushed with nitrogen, sealed and treated at 120° C. for 10 min in the microwave. Water (20 ml) was added to the mixture. The crystalline solid was taken by filtration and washed with water (2×10 ml), ethanol (2×10 ml) and ether (2×10 ml). The solid was then dissolved in chloroform and treated in the usual manner to afford a yellow solid. Yield 32 (95 mg, 0.218 mmol, 58.3%): $^1$H NMR (CDCl$_3$) δ: 1.92(m, 4H), 2.23(s, 12H), 2.43(m, 4H), 4.27(m, 4H), 8.75(s, 4H); $^{13}$C NMR (CDCl$_3$) δ: 26.00(2×CH$_2$), 39.38(2×CH$_2$), 45.38(4×CH$_3$), 57.24(2×CH$_2$), 126.66(4×0), 126.70(2×0), 130.87(4×CH), 162.83(4×C═O); HRMS (ES+) calcd C$_{24}$H$_{28}$N$_4$O$_4$ [M+H]$^+$ 437.2183. Found: 437.2197.

N,N'-bis(3-(dimethylamino)ethylamino)-1,4,5,8-naphthalenetetracarboxylic acid diimide (33) (Prior Art)

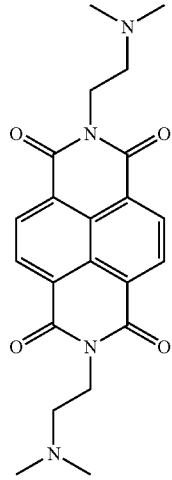

Naphthalene dianhydride (100 mg, 0.373 mmol) was suspended in N,N-dimethyl-1,2-ethanediamine (2 ml) in a microwave reaction vessel. The tube was flushed with nitrogen, sealed and treated at 120° C. for 10 min in the microwave. Water (20 ml) was added to the mixture. The crystalline solid was taken by filtration and washed with water (2×10 ml), ethanol (2×10 ml) and ether (2×10 ml). The solid was then dissolved in chloroform and treated in the usual manner to afford a yellow solid. Yield 33 (105 mg, 0.257 mmol, 68.9%): $^1$H NMR (CDCl$_3$) δ: 2.34(s, 12H), 2.66(t, 4H, J=6.8 Hz), 4.34(t, 4H, J=6.8 Hz), 8.74(s, 4H); $^{13}$C NMR (CDCl$_3$) δ: 38.68(2×CH$_2$), 45.78(4×CH$_3$), 56.96(2×CH$_2$), 126.63(2×C), 126.76(4×C), 130.95(4×CH), 162.88(4×C═O); HRMS (ES+) calcd C$_{22}$H$_{24}$N$_4$O$_4$ [M+H]$^+$ 409.1870. Found: 409.1861.

Purities of the Final Compounds

The purity of the final compounds was quantified by HPLC using two different analytical methods (as described in the "general methods" section). Details are given in Table 1 below:

TABLE 1

| Compound | Purity Method A (%) | Purity Method B (%) | Average Purity (%) |
|---|---|---|---|
| 8 | 99.7 | 99.71 | 99.705 |
| 9 | 97.07 | 100 | 98.535 |
| 12 | 95.62 | 99.79 | 97.7 |
| 13 | 91.11 | 98.89 | 95 |
| 14 | 93.36 | 94.84 | 94.1 |
| 15 | 95.11 | 98.65 | 96.88 |
| 16 | 92.87 | 95.65 | 94.2 |
| 17 | 92.37 | 81.05 | 86.71 |
| 18 | 92.43 | 97.12 | 94.77 |
| 19 | 94.28 | 98.24 | 96.26 |
| 20 | 99.76 | 100 | 99.88 |
| 21 | 98.02 | 99.97 | 98.99 |
| 22 | 98.44 | 100 | 99.22 |
| 23 | 94.98 | 97.55 | 96.26 |
| 24 | 94.54 | 100 | 97.27 |
| 25 | 74.56 | 78.69 | 76.625 |
| 26 | 97.02 | 98.06 | 97.54 |
| 27 | 97.03 | 98.6 | 97.815 |
| 28 | 90.34 | 91.45 | 90.895 |
| 29 | 99.43 | 90.14 | 94.785 |
| 30 | 98.64 | 95.45 | 97.045 |
| 31 | 98.61 | 99.27 | 98.94 |
| 32 | 96.81 | 98.47 | 97.64 |
| 33 | 99.28 | 98.79 | 99.035 |

Example 2 a) FRET Assay

The appropriate tagged DNA: 5'-FAM-d(GGG[TTA GGG]$_3$-TAMRA-3' for the telomeric G-quadruplex; 5'-FAM-dTATAGCTATA-HEG-TATAGCTATA-TAMRA-3' (HEG linker: [(—CH2-CH2-O—)6]) for the duplex DNA; 5'-FAM-AGAGGGAGGGCGCTGGGAGGAGGGGCT-TAMRA-3' for the ckit1 G-quadruplex; or 5'-FAM-CCCGGGCGGGCGCGAGGGAGGGGAGG-TAMRA-3' for the ckit2 G-quadruplex (all purchased from Eurogentec, Southhampton, UK); was diluted to 400 nM using FRET buffer (50 mM potassium cacodylate pH 7.4) and annealed by heating at 85° C. for 5 min and cooling down to RT over 5 h. Compound dilutions were prepared in a concentration of twice the final concentration using FRET buffer from the 1 mM stock solutions. 50 μL of annealed DNA and 50 μL of compound per well were put into 96-well plates and processed in a DNA Engine Opticon (MJ Research). Fluorescence readings were taken at intervals of 0.5° C. over the range 30-100° C., with a constant temperature being maintained for 30 seconds prior to each reading. Irradiation was at 450-495 nm and detection at 515-545 nm. The raw data were imported into Origin 7.0 (OriginLab Corp.) and the graphs smoothed using a 10-point running average and subsequently normalised. For the determination of the melting temperature, the first derivative of the smoothed melting curve was calculated. The difference between the melting temperature at 0.5 µM of the compound and the melting temperature for the blank ($\Delta T_m(0.5\ \mu M)$) was used for comparison.

b) TRAP Assay

The TRAP assay was carried out in three steps with an initial primer elongation step by telomerase, a subsequent removal of the primer bound ligand and a final PCR amplification of the telomerase products.

The first step of the TRAP assay was carried out by preparing a master mix containing the TS forward primer (0.1 µg; 5'-AAT CCG TCG AGC AGA GTT-3'), TRAP buffer (20 mM Tris-HCl [pH 8.3], 68 mM KCl, 1.5 mM $MgCl_2$, 1 mM EGTA, 0.05% v/v Tween-20), bovine serum albumin (0.05 µg), and dNTPs (125 µM each), protein extract (500 µg/sample) diluted in lysis buffer (10 mM Tris-HCl, pH 7.5, 1 mM $MgCl_2$, 1 mM EGTA, 0.5% CHAPS, 10% Glycerol, 5 mM β-mercaptoethanol, 0.1 mM AEBSF).

The PCR master mix was added to tubes containing freshly prepared compounds at various concentrations and to the negative control containing no drug. The initial elongation step was carried out for 10 min at 30° C., followed by a 94° C. for 5 min and a final maintenance of the mixture at 20° C.

To purify the elongated product and to remove the bound ligands the QIAquick nucleotide purification kit (Qiagen) was used according to manufacturer's instructions. The kit is especially designed for the purification of both double and single-stranded oligonucleotides from 17 bases in length. The kit employs a high salt concentration buffer to bind the negatively charged oligos to the positively charged spin-tube membrane through centrifugation. An ethanol based buffer is then used to wash any impurities away before elution of the DNA using a low salt concentration solution. This was substituted with PCR-grade water in our experiments.

The purified extended samples were then subject to PCR amplification. For this, a second PCR master mix was prepared consisting of ACX reverse primer (1 µM; 5'-GCG CGG [CTTACC]3 CTA ACC-3'), TS forward primer (0.1 µg; 5'-AAT CCG TCG AGC AGA GTT-3'), TRAP buffer, BSA (5 µg), 0.5 mM dNTPs and 2 U of taq polymerase. An aliquot of 10 µl of the master mix was added to the purified telomerase extended samples and amplified at: 35 cycles of 94° C. for 30 sec, 61° C. for 1 min and 72° C. for 1 min. samples were separated on a 12% PAGE and visualised with Sybregreen staining. Fluorescence from drug samples were normalised against positive control containing protein only. All samples were corrected for background by subtracting the fluorescence reading of negative controls.

c) Cell Culture

General:

Human cancer cell lines, breast (MCF7), lung (A549), colon (HT-29), gastric (HGC-27) and normal human lung fibroblast lines (WI-38) were purchased from American Type Cell Culture (ATCC). The GIST882 line was a gift from Dr Jonathan Fletcher. All cell lines except HGC27 and WI38 were maintained in Dulbecco's Modified Eagles Media containing 10% foetal bovine serum (Invitrogen, UK), 0.5 mg/ml hydrocortisone (Acros Chemicals, Loughborough, UK), 2 mM L-glutamine (Invitrogen, Netherlands), and non-essential amino-acids (Invitrogen, Netherlands), and incubated at 37° C., 5% $CO_2$. The WI38 and HGC27 lines were maintained in minimum essential medium, prepared as above. All cell lines were routinely passaged at a ratio of 1:6.

SRB Toxicity Assay

Short-term growth inhibition was measured using the SRB assay as described previously. Briefly, cells were seeded (4000 cells/wells) into the wells of 96 well-plates in appropriate medium and incubated overnight to allow the cells to attach. Subsequently cells were exposed to freshly-made solutions of drugs and incubated for a further 96 h. Following this the cells were fixed with ice cold trichlo-acetic acid (TCA) (10%, w/v) for 30 min and stained with 0.4% SRB dissolved in 1% acetic acid for 15 min. All incubations were carried out at room temperature. The $IC_{50}$ value, concentration required to inhibit cell growth by 50%, was determined from the mean absorbance at 540 nm for each drug concentration expressed as a percentage of the control untreated well absorbance.

Senescence Studies

Senescence detection and quantification experiments were carried out using a commercially available kit (Senescence β-galactosidase staining kit, Cell Signalling Technology, MA, USA). $1 \times 10^5$ cells were seeded in a 35 mm well of a 6-well plate (Nunc, Denmark) in 2 ml of medium and compound to test. The cells were incubated for 24 hours. The medium was then removed and the cells were washed with PBS (1×2 ml). The cells were fixed by treating them with 1 ml of fixative solution (2% formaldehyde and 2% glutaraldehyde in PBS) for 15 minutes at RT. The fixative solution was then removed and the wells washed with PBS (2×2 ml). Freshly prepared staining solution (a mixture of 930 µL of 40 mM citric acid/sodium phosphate (pH 6.0), 0.15 M NaCl and 2 mM $MgCl_2$, 10 µL of 500 mM potassium ferrocyanide, 10 µL of 500 mM potassium ferricyanide and 50 µL of 20 mg/ml 5-bromo-4-chloro-3-indolyl-µD-galactopyranoside in DMF) (1 ml) was added and the cells were incubated overnight. The senescent cells, detected by their blue pigmentation, were quantified under a light microscope.

The results are shown in Tables 2 and 3.

TABLE 2

Toxicity and Senescence data table

| Compound | MCF7 | A549 | $IC_{50}$ (nM) W138 | HT-29D | HGC-27 | GIST882 | Senescence (% of cells) after 1 week (MCF7) |
|---|---|---|---|---|---|---|---|
| 8 | 26.9 | 57.1 | 57.7 | n.a. | n.a. | n.a. | n.a. |
| 9 | 287.7 | 1700 | 10000 | n.a. | n.a. | n.a. | n.a. |
| 12 | 104.7 | 28.7 | 292.3 | 63 | 510 | 1300 | 35.0 ± 3 (at 70 nM) |
| 13 | 5.4 | 13.3 | 42.8 | n.a. | n.a. | n.a. | n.a. |
| 14 | 9.2 | 15.3 | 40.12 | n.a. | n.a. | n.a. | n.a. |
| 15 | 18.5 | 25.09 | 137.5 | n.a. | n.a. | n.a. | n.a. |
| 16 | 18 | 10.7 | 86.7 | 20 | 170 | n.a. | n.a. |
| 17 | 17.9 | 48 | 83.7 | n.a. | n.a. | n.a. | 35 ± 3 (at 15 nM) |
| 18 | 219 | 273.9 | 971.9 | 81 | 480 | 530 | n.a. |
| 19 | 164.4 | 144 | 466.8 | 35 | 68 | n.a. | n.a. |

TABLE 2-continued

Toxicity and Senescence data table

| Compound | MCF7 | A549 | IC$_{50}$ (nM) W138 | HT-29D | HGC-27 | GIST882 | Senescence (% of cells) after 1 week (MCF7) |
|---|---|---|---|---|---|---|---|
| 20 | 295.7 | 204.5 | 1460 | n.a. | n.a. | n.a. | n.a. |
| 21 | 128.9 | 145.6 | 438.9 | n.a. | n.a. | n.a. | n.a. |
| 22 | 10.2 | 13.6 | 63.4 | 15 | 41 | 1600 | n.a. |
| 23 | 11 | 18.3 | 63.9 | n.a. | n.a. | n.a. | n.a. |
| 24 | 81.3 | 115.3 | 167.2 | n.a. | n.a. | n.a. | 45 ± 6 (at 75 nM) |
| 25 | 10.5 | 96 | 62.6 | n.a. | n.a. | n.a. | n.a. |
| 26 | 8300 | >10000 | >10000 | n.a. | n.a. | n.a. | n.a. |
| 27 | 9200 | >10000 | >10000 | n.a. | n.a. | n.a. | n.a. |
| 28 | 437 | 1190 | 965 | n.a. | n.a. | n.a. | n.a. |
| 29 | 800 | 1320 | 1220 | n.a. | n.a. | n.a. | n.a. |
| 30 | 6700 | >10000 | >10000 | n.a. | n.a. | n.a. | 51 ± 3 (at 3.5 µm) |
| 31 | 1610 | 2750 | 8500 | n.a. | n.a. | n.a. | n.a. |
| 32 | 135.2 | 113.8 | 210.9 | n.a. | n.a. | n.a. | n.a. |
| 33 | 118.9 | 99.1 | 171.1 | n.a. | n.a. | n.a. | n.a. | n.a. = Not available.

TABLE 3

FRET and TRAP data table

| Comp. | FRET-Q[a] (° C.) ΔTm(0.5 µM) | FRET-d[b] (° C.) ΔTm(0.5 µM) | FRET-ckit1[c] (° C.) ΔTm(0.5 µM) | FRET-ckit2[d] (° C.) ΔTm(0.5 µM) | TRAP EC$_{50}$ (µM) |
|---|---|---|---|---|---|
| 8 | 27.7 | 0.2 | 0 | 4.25 | n.a.[e] |
| 9 | 23.7 | 3.5 | 18 | 24 | n.a. |
| 12 | 33.2 | 4.5 | 29.75 | 36.5 | 25 ± 2.5 |
| 13 | 26.5 | 12.5 | 23.5 | 29 | 17 ± 1.1 |
| 14 | 28 | 7.5 | 25.25 | 29.75 | n.a. |
| 15 | 17.2 | 4.2 | 12 | 18.75 | n.a. |
| 16 | 35.2 | 4.2 | 33.75 | 36.25 | 21.3 ± 1.1 |
| 17 | 26.2 | 11.5 | 24.5 | 28.5 | 27.9 ± 0.4 |
| 18 | 30 | 4 | 27.25 | 31.25 | n.a. |
| 19 | 21 | 5 | 16.25 | 24.25 | n.a. |
| 20 | 27.5 | 2.2 | 20.25 | 20.5 | n.a. |
| 21 | 17.5 | 4.7 | 15.75 | 20 | n.a. |
| 22 | 29.7 | 3.5 | 27 | 32 | 12.3 |
| 23 | 21.2 | 6.5 | 18.25 | 24.25 | n.a. |
| 24 | 34.5 | 2 | 31.5 | 39.25 | 21.0 ± 8.8 |
| 25 | 28.2 | 10.7 | 25.75 | 31.5 | n.a. |
| 26 | 14.2 | −0.5 | −0.75 | 6 | n.a. |
| 27 | 10.5 | −0.5 | 0.75 | 4.75 | n.a. |
| 28 | 20.5 | 3.7 | 16 | 15.75 | n.a. |
| 29 | 10.2 | 3.2 | 12 | 9.25 | n.a. |
| 30 | 13.7 | 3 | 1 | 8.5 | >50 |
| 31 | 6.2 | 3 | 2 | 5.5 | n.a. |
| 32 | 5.2 | 2.7 | 2.5 | 7.75 | n.a. |
| 33 | 3.2 | 1 | 1.25 | 7.25 | n.a. |

[a]FRET data for telomeric G-quadruplex sequence (maximum error ± 1° C.).
[b]FRET data for duplex sequence (maximum error ± 1° C.).
[c]FRET data for ckit1 G-quadruplex sequence (maximum error ± 1° C.).
[d]FRET data for ckit2 G-quadruplex sequence (maximum error ± 1° C.).
[e]Not available.

Discussion of Results

The initial assessment of the DNA stabilisation ability of the compounds was done using FRET. Four different DNA sequences were used—a model for the human telomeric G-quadruplex, a self-complementary duplex DNA hairpin and two sequences that are present in the promoter region of the CKIT gene. A FRET competition experiment was also run in which affinity for the telomeric G-quadruplex sequence was evaluated in presence of increasing concentrations of duplex DNA. These experiments allowed us to assess the selectivity of the ligands between quadruplex and duplex DNA. The results of FRET are shown in Table 3.

The stabilisation ability of the compounds towards the G-quadruplex DNA sequences was excellent. For some, concentrations of 0.5 µM were sufficient to increase the melting temperature by 35° C. This level of stabilisation with BRACO19 (a conventional G-quadruplex ligand) requires a concentration of 2.5 µM. The values of ΔTm at 0.5 µM (ΔTm (0.5 µM)) were used for comparison as for some compounds the 1 µM concentration normally used was enough to completely avoid melting of the DNA. Consistently for the whole series, the tetrasubstituted ligands performed better than the tri- and these better than the disubstituted counterparts. There is a structural benefit in the use of four side chains, regardless of the overall number of charges, as this effect is observed too for compounds 28/29, 30/31 and 26/27, neutral at pH 7. Compounds 12, 16 and 24 and 13, 17 and 25 have the highest ΔTm of all within the 4-ND and 3-ND series respectively. They all have side chains of the same length (3 carbons) and similar end groups (protonated at pH 7 tertiary amines). Substitution of the tertiary amines for morpholino groups for compounds reduces the ΔTm. However, the morpholino and also the hydroxyl analogues 26 and 27 have good stabilisation ability also.

Most ligands showed a certain degree of interaction of with duplex DNA. Compounds 26 and 27 however, slightly destabilised this sequence. With the exception of the pair of compounds 14/15, the trisubstituted are stronger binders to the duplex DNA that the tetrasubstituted analogues, probably because of steric reasons.

In the competition experiments tetrasubstituted compounds (4-ND) showed better selectivity towards the G-quadruplex than the other analogues. 4-ND retained 100% stabilisation ability at the 1:1 competition experiments, unlike the di- or trisubstituted analogues (2-ND and 3-ND respectively) for which a reduction of the ability was observed (5-25%). The results are shown in FIG. 4. Compounds 18 and 19 retained a higher level of stabilisation (100% for 18 and 60% for 19) at the 1:10 experiment when compared to the rest of 4-ND (30-70% retention, except for 26) and 3-ND (30-40% retention, except for 25 and 27). 4-ND perform better at the 1:100 and 1:300 experiments with retention of the ability of 10-40% and 10-30% respectively (100% retention for 26). On the other hand most 2-ND and 3-ND lost almost completely any stabilisation ability (<10% retention) in these experiments. Interestingly the compounds with hydroxyl groups 26 and 27, unlike the rest of compounds, presented no (26) or very little (15% for 27) loss of stabilisation ability at the 1:300 experiments.

A group of ligands were also evaluated as telomerase inhibitors using a modified TRAP assay (see Table 3 for results). Values of $EC_{50}$ between 12 and 28 µM were obtained with the exception of compound 30 (>50 µM). No correlation could be obtained between FRET and TRAP data but compound 30 is the worst ligand in FRET in the group.

The toxicity of the compounds against the panel of cell lines was assessed using the SRB assay. The compounds showed a very strong potency, especially towards the cancer cell lines. The results are shown in Table 2.

The onset of senescence as a result of telomere damage is a well reported event. Senescence phenotype was investigated in MCF7 cells treated for 1 week with sub-cytotoxic concentrations of a selection of compounds. All the compounds used in this study showed a significant increase in % of senescence cells after treatment.

G-quadruplex interacting agents may cause telomere uncapping which may result in the fusion of two independent chromosomes. We prepared chromosome spreads of cells under the same treatment that caused the onset of senescence but we failed to detect any abnormal level of fusions.

The tri- and tetrasubstituted compounds, like other naphthalene diimide compounds, presented fluorescent properties. This allowed us to use the natural occurring florescence of a selected group of compounds to detect their localisation within MCF7 cells using confocal microscopy. Compounds 12, 17 and 24 were shown to localise exclusively in the nucleus upon exposure of 30 minutes at 0.5 µM concentrations (FIG. 5-1). For compound 30 however a less intense and homogeneously distributed signal was observed upon treatment with up to 50 µM (FIG. 5-2). The compounds that concentrated in the nucleus showed preference for the nucleolus (FIG. 5-3).

REFERENCES

[1]=Hopkins, H et al, Journal of Solution Chemistry 1986, 15, 563-579
[2]=Sissi, C et al, Bioorg. Med. Chem. 2007, 15, 555-562
[3]=Braña et al, Curr. Med. Chem., Anti-Cancer Agents, 2001, 1, 257-255
[4]=Thalacker et al, J. Org. Chem. 2006, 71, 8098-8105
[5]=US 2003/0153005

The invention claimed is:

1. A pharmaceutical composition comprising a compound that is of general formula (I) or is a salt, solvate, or prodrug thereof,

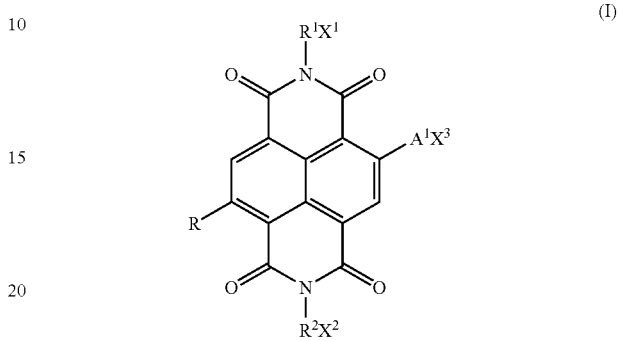

wherein $R^1$ and $R^2$ are each independently divalent radicals selected from $C_{1-20}$ alkyl, $C_{2-20}$ alkenyl, $C_{7-20}$ alkaryl, $C_{2-10}$ alkynyl, $C_{7-20}$ aralkyl, $C_{2-20}$ heteroaralkyl, $C_{3-30}$ heterocyclylalkyl, $C_{3-30}$ alkylheterocyclyl, $C_{3-20}$ cycloalkyl, $C_{3-20}$ heterocyclyl, $C_{2-20}$ heteroaryl, $C_{5-20}$ aryl and $C_{1-10}$ alkoxy;

R is H or $A^2X^4$;

wherein $X^1$-$X^4$ are each independently selected from halo, OH, $OR^3$, COH, $NH_2$, $NHR^3$, $NR^3R^4$, COOH, $CONH_2$, $COOR^3$, $CONHR^3$, $CONR^3R^4$, SH, $SR^3$, $COR^3$ and cyano, provided that at least one of groups $X^1$-$X^4$ is a tertiary amine;

wherein $R^3$ and $R^4$ are independently selected from $C_{1-6}$ alkyl, $C_{6-20}$ aryl, and $C_{7-20}$ aralkyl or $R^3$ and $R^4$ together with the nitrogen atom to which they are attached form a 3-8 membered ring, which is optionally substituted and optionally comprises other hetero atoms;

$A^1$ and $A^2$ are each independently selected from $NHR^5$;

wherein $R^5$ is a divalent radical selected from $C_{1-20}$ alkyl, $C_{6-20}$ aryl, $C_{7-20}$ alkaryl and $C_{7-20}$ aralkyl;

wherein any of the groups $R^1$-$R^5$, $A^1$ and $A^2$ may be substituted with $C_{1-20}$ alkyl, $C_{2-20}$ alkenyl, $C_{7-20}$ alkaryl, $C_{2-10}$ alkynyl, $C_{7-20}$ aralkyl, $C_{2-20}$ heteroaralkyl, $C_{3-30}$ heterocyclylalkyl, $C_{3-30}$ alkylheterocyclyl, $C_{3-20}$ cycloalkyl, $C_{3-20}$ heterocyclyl, $C_{2-20}$ heteroaryl, $C_{5-20}$ aryl or $C_{1-10}$ alkoxy, halo, OH, $OR^3$, COH, $NH_2$, $NHR^3$, $NR^3R^4$, COOH, $CONH_2$, $COOR^3$, $CONHR^3$, $CONR^3R^4$, SH, $SR^3$, $COR^3$ or cyano; and wherein the pharmaceutical composition also comprises a pharmaceutically acceptable carrier.

2. The pharmaceutical composition according to claim 1 wherein R is H.

3. The pharmaceutical composition according to claim 1 wherein R is $A^2X^4$.

4. The pharmaceutical composition according to claim 1 wherein $R^1x^1$=$R^2X^2$.

5. The pharmaceutical composition according to claim 3 wherein $X^1$-$X^4$ are selected from $NH_2$, $NR^3R^4$, OH, $OR^3$ and $NHR^3$.

6. The pharmaceutical composition according to claim 5 wherein $X^1$-$X^4$ are $NR^3R^4$, wherein $R^3$ and $R^4$ are independently methyl or ethyl.

7. The pharmaceutical composition according to claim 5 wherein $X^1$-$X^4$ are $NR^3R^4$, wherein $R^3$ and $R^4$ together with the nitrogen-atom to which they are attached form a 5 or 6 membered ring.

8. The pharmaceutical composition according to claim 7 wherein the group $NR^3R^4$ is pyrrolidine, piperidine or morpholine.

9. The pharmaceutical composition according to claim 1 comprising a prodrug of a compound of formula (I), wherein groups $X^1$-$X^4$ of the prodrug are N-oxides or $N^+(\text{—}O^-)R^3R^4$.

10. The pharmaceutical composition according to claim 1 wherein $R^1$ and $R^2$ are divalent radicals selected from $C_{1-10}$ alkyl.

11. The pharmaceutical composition according to claim 1 wherein $R^5$ is a divalent radical selected from $C_{1-10}$ alkyl.

12. The pharmaceutical composition according to claim 3 wherein at least one of $A^1X^3$ and $A^2X^4$ has the structure

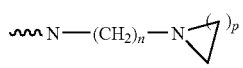

wherein n is 1-4 and p is 2-6.

13. A compound that is of general formula (I) or is a salt, solvate, or prodrug thereof

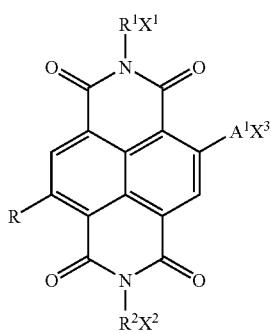

wherein $R^1$ and $R^2$ are each independently divalent radicals selected from $C_{1-20}$ alkyl, $C_{2-20}$ alkenyl, $C_{7-20}$ alkaryl, $C_{2-10}$ alkynyl, $C_{7-20}$ aralkyl, $C_{2-20}$ heteroaralkyl, $C_{3-30}$ heterocyclylalkyl, $C_{3-30}$ alkylheterocyclyl, $C_{3-20}$ cycloalkyl, $C_{3-20}$ heterocyclyl, $C_{2-20}$ heteroaryl, $C_{5-20}$ aryl and $C_{1-10}$ alkoxy;
R is H or $A^2X^4$;
wherein $X^1$-$X^4$ are each independently selected from halo, OH, $OR^3$, COH, $NH_2$, $NHR^3$, $NR^3R^4$, COOH, $CONH_2$, $COOR^3$, $CONHR^3$, $CONR^3R^4$, SH, $SR^3$, $COR^3$ and cyano, provided that at least one of groups $X^1$-$X^4$ is a tertiary amine;
wherein $R^3$ and $R^4$ are independently selected from $C_{1-6}$ alkyl, $C_{6-20}$ aryl, and $C_{7-20}$ aralkyl or $R^3$ and $R^4$ together with the nitrogen atom to which they are attached form a 3-8 membered ring, which is optionally substituted and optionally comprises other hetero atoms;
$A^1$ and $A^2$ are each independently selected from $NHR^5$;
wherein $R^5$ is a divalent radical seleced from $C_{1-20}$ alkyl, $C_{6-20}$ aryl, $C_{7-20}$ alkaryl and $C_{7-20}$ aralkyl;
wherein any of the groups $R^1$-$R^5$, $A^1$ and $A^2$ may be substituted with $C_{1-20}$ alkyl, $C_{2-20}$ alkenyl, $C_{7-20}$ alkaryl, $C_{2-10}$ alkynyl, $C_{7-20}$ aralkyl, $C_{2-20}$ heteroaralkyl, $C_{3-30}$ heterocyclylalkyl, $C_{3-30}$ alkylheterocyclyl, $C_{3-20}$ cycloalkyl, $C_{3-20}$ heterocyclyl, $C_{2-20}$ heteroaryl, $C_{5-20}$ aryl or $C_{1-10}$ alkoxy, halo, OH, $OR^3$, COH, $NH_2$, $NHR^3$, $NR^3R^4$, COOH, $CONH_2$, $COOR^3$, $CONHR^3$, $CONR^3R^4$, SH, $SR^3$, $COR^3$ or cyano.

14. A compound according to claim 13 wherein R is H.

15. A compound according to claim 13 wherein R is $A^2X^4$.

16. A compound according to claim 13 wherein $R^1X^1$=$R^2X^2$.

17. A compound according to claim 15 wherein $X^1$-$X^4$ are selected from $NH_2$, $NR^3R^4$, OH, $OR^3$ and $NHR^3$.

18. A compound according to claim 17 wherein $X^1$-$X^4$ are $NR^3R^4$, wherein $R^3$ and $R^4$ are independently methyl or ethyl.

19. A compound according to claim 17 wherein $X^1$-$X^4$ are $NR^3R^4$, wherein $R^3$ and $R^4$ together with the nitrogen-atom to which they are attached form a 5 or 6 membered ring.

20. A compound according to claim 19 wherein the group $NR^3R^4$ is pyrrolidine, piperidine or morpholine.

21. A compound according to claim 13 which is a prodrug of a compound of formula (I), wherein groups $X^1$-$X^4$ of the prodrug are N-oxides or $N^+(\text{—}O^-)R^3R^4$.

22. A compound according to claim 13 wherein $R^1$ and $R^2$ are divalent radicals selected from $C_{1-10}$ alkyl.

23. A compound according to claim 13 wherein $R^5$ is a divalent radical selected from $C_{1-10}$ alkyl.

24. A compound according to claim 15 wherein at least one of $A^1X^3$ and $A^2X^4$ the structure

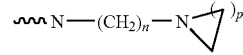

wherein n is 1-4 and p is 2-6.

25. The pharmaceutical composition according to claim 7 wherein the 5 or 6 membered ring contains an oxygen atom.

26. The pharmaceutical composition according to claim 10 wherein $R^1$ and $R^2$ are divalent radicals selected from $C_{2-4}$ alkyl.

27. The pharmaceutical composition according to claim 11 wherein $R^5$ is a divalent radical selected from $C_{2-4}$ alkyl.

28. A compound according to claim 19 wherein the 5 or 6 membered ring contains an oxygen atom.

29. A compound according to claim 22 wherein $R^1$ and $R^2$ are divalent radicals selected from $C_{2-4}$ alkyl.

30. A compound according to claim 23 wherein $R^5$ is a divalent radical selected from $C_{2-4}$ alkyl.

* * * * *